(12) United States Patent
Adler, Jr.

(10) Patent No.: US 8,592,158 B2
(45) Date of Patent: Nov. 26, 2013

(54) DETECTING MULTINUCLEOTIDE REPEATS

(75) Inventor: Karl Edwin Adler, Jr., Hampton Falls, NH (US)

(73) Assignee: PerkinElmer Health Sciences, Inc., Waltham, MA (US)

( * ) Notice: Subject to any disclaimer, the term of this patent is extended or adjusted under 35 U.S.C. 154(b) by 487 days.

(21) Appl. No.: 12/834,633

(22) Filed: Jul. 12, 2010

(65) Prior Publication Data

US 2011/0014621 A1 Jan. 20, 2011

Related U.S. Application Data

(60) Provisional application No. 61/224,651, filed on Jul. 10, 2009, provisional application No. 61/288,518, filed on Dec. 21, 2009.

(51) Int. Cl.
*C12Q 1/68* (2006.01)
*C07H 21/04* (2006.01)

(52) U.S. Cl.
USPC ........................................ 435/6.12; 536/24.31

(58) Field of Classification Search
None
See application file for complete search history.

(56) References Cited

U.S. PATENT DOCUMENTS

| | | | |
|---|---|---|---|
| 7,414,115 B2 | 8/2008 | Livak et al. | |
| 2005/0191636 A1* | 9/2005 | Hahn | 435/6 |
| 2008/0113355 A1 | 5/2008 | Hagerman et al. | |
| 2008/0124709 A1 | 5/2008 | Huang et al. | |
| 2009/0136956 A1 | 5/2009 | Merante et al. | |

OTHER PUBLICATIONS

Wilson, J. et al., Consensus Characterization of 16 *FMR1* Reference Materials: A Consortium Study, *Journal of Molecular Diagnostics*, 10(1): 2-12, Jan. 2008.
Fojta, M. et al., Electrochemical Detection of DNA Triplet Repeat Expansion, *J. Am. Chem. Soc.*, 126: 6532-33, 2004.

* cited by examiner

*Primary Examiner* — Prabha Chunduru
(74) *Attorney, Agent, or Firm* — Gifford, Krass, Sprinkle, Anderson & Citkowski, P.C.

(57) ABSTRACT

Methods of determining the length of a multinucleotide repeat region in a target nucleic acid are provided herein which include labeling amplified target nucleic acids with a target detection label independent of the number of multinucleotide repeats and a repeat-detection label proportional to the number of multinucleotide repeats, wherein the two types of labels are each independently incorporated in the amplified target nucleic acids during the amplifying or after the amplifying; binding the amplified target nucleic acids to a capture probe specific for the amplified target nucleic acids; detecting the target detection label associated with the capture probe to produce a first signal; detecting the repeat-detection label associated with the capture probe to produce a second signal; and determining a ratio of the first signal and the second signal, wherein the ratio is indicative of the length of the multinucleotide repeat region in the target nucleic acid.

14 Claims, 13 Drawing Sheets

DETECTING MULTINUCLEOTIDE REPEATS

REFERENCE TO RELATED APPLICATIONS

This application claims priority to U.S. Provisional Patent Application Ser. Nos. 61/224,651, filed Jul. 10, 2009 and 61/288,518, filed Dec. 21, 2009, the entire content of both of which is incorporated herein by reference.

FIELD OF THE INVENTION

Methods described generally relate to assays for determining the extent of multinucleotide repeat regions in a target nucleic acid. In specific aspects, described methods relate to assays for determining the extent of multinucleotide repeats in a target nucleic acid in which amplified target nucleic acids are labeled with a first label which is independent of the number of multinucleotide repeats and a second label which is proportional to the number of multinucleotide repeats in order to determine a ratio between signals detected from the labels which is indicative of the number of multinucleotide repeats.

BACKGROUND OF THE INVENTION

Several constitutional disorders in humans are characterized by an expanded region of trinucleotide repeats in a particular locus of an individual's genome. The two best-known disorders of this type are Fragile X syndrome and Huntington's disease. The number of trinucleotide repeats present at the locus of an individual's genome correlates with the severity of the disorder. Thus, various methods have been developed for determining the length of a trinucleotide repeat region of certain disorder-related genes. In Fragile X, the repeat motif is CGG. The established clinical method for diagnosis of Fragile X is the Southern blot, in which genomic DNA from an individual is digested by a restriction enzyme to excise the trinucleotide repeat region from the genomic DNA. This trinucleotide repeat region is then size-separated by electrophoresis on an agarose gel, blotted onto a membrane, and the membrane probed with a labeled probe specific to the Fragile X locus. This method utilizes the size separation capability of electrophoresis to measure the size of the repeat region, and is labor intensive, time consuming, and requires subjective interpretation of fragment size.

Other published methods for determining the length of a trinucleotide repeat region involve amplifying the target region by PCR followed by size evaluation by capillary electrophoresis using a sequencing instrument. PCR of the target region is performed using primers that straddle the repeat region. The PCR has been optimized to amplify up to 1,000 or more repeats with the best of these methods.

Interpreting electrophoresis results on a conventional planar gel can be challenging. The size reading is somewhat subjective and involves comparing excursion distances between a standard and a sample, assuming insignificant distortion across the gel. One PCR-gel method utilizes repeat primers, in which the primers are full or partial complements of the repeat motif of the target. Electrophoresis of PCR products made with repeat primers results in a smear; the products are a mixture of many different products of different lengths. Interpreting these repeat-primer PCR electrophoresis images is subjective.

Another published method utilizes repeat primers as an alternate to the straddle primers, with high-resolution evaluation on a capillary sequencing instrument. While resolution and clarity of results are improved vs. the planar electrophoresis interpretation can be challenging, particularly in cases of PCR stutter.

All of the methods that utilize capillary sequencing instruments as the reading mechanism are limited by the high cost of those instruments, and by the fact that their operation (such as ambient temperature range) and maintenance requirements are quite stringent.

SUMMARY OF THE INVENTION

Methods of determining the length of a multinucleotide repeat region in a target nucleic acid are provided herein which include amplifying a target nucleic acid containing a multinucleotide repeat region to produce amplified target nucleic acids; labeling the amplified target nucleic acids with a first label and a second label, the first label independent of the number of multinucleotide repeats and the second label proportional to the number of multinucleotide repeats, wherein the first and second labels are each independently incorporated in the amplified target nucleic acids during the amplifying or after the amplifying; binding the amplified target nucleic acids to a capture probe specific for the amplified target nucleic acids; detecting the first label associated with the capture probe to produce a first signal; detecting the second label associated with the capture probe to produce a second signal; and determining a ratio of the first signal and the second signal, wherein the ratio is indicative of the length of the multinucleotide repeat region in the target nucleic acid.

According to embodiments of described methods, binding of the amplified target nucleic acids comprises specific hybridization of the amplified target nucleic acids to complementary nucleic acid capture probes.

Optionally, the first label is incorporated in a straddle primer used in amplifying the target nucleic acid In further options, the second label is present in nucleotides used in amplifying the target nucleic acid to produce the amplified target nucleic acids or present in probes which specifically bind to multinucleotide repeats in the amplified target nucleic acids. For example, probes which specifically bind to multinucleotide repeats in the amplified target nucleic acids are nucleic acid probes complementary to the multinucleotide repeats in the amplified target nucleic acids.

The target nucleic acid is isolated from a biological sample according to embodiments of methods provided herein. The term "isolated" refers to separation of the nucleic acids from at least some components of the environment in which they are naturally found. Thus, for example, isolated nucleic acids may be separated from cellular debris.

Methods are described herein in which the target nucleic acid is genomic DNA.

A biological sample is obtained from an individual subject, such as, but not limited to, a human subject for use in methods described herein.

For example, a biological sample used according to embodiments described herein is obtained from individual subject having or is at risk of having a trinucleotide repeat expansion disorder selected from the group consisting of: Dentatorubropallidoluysian atrophy, Huntington's disease, spinobulbar muscular atrophy, spinocerebellar ataxia type 1, spinocerebellar ataxia type 2, spinocerebellar ataxia type 3, spinocerebellar ataxia type 6, spinocerebellar ataxia type 7, spinocerebellar ataxia type 17, fragile X syndrome; fragile XE mental retardation; Friedreich's ataxia; myotonic dystrophy; spinocerebellar ataxia type 8 and spinocerebellar ataxia type 12.

Methods described herein include amplifying a reference nucleic acid multinucleotide repeat region to produce amplified target reference nucleic acids according to some embodiments. Such methods further include labeling the amplified target reference nucleic acids with a first label and a second label, the first label independent of the number of multinucleotide repeats and the second label proportional to the number of multinucleotide repeats, wherein the first and second labels are each independently incorporated in the amplified target reference nucleic acids during the amplifying or after the amplifying; binding the amplified target reference nucleic acids to a capture probe specific for the amplified target reference nucleic acids; detecting the first label associated with the capture probe to produce a third signal; detecting the second label associated with the capture probe to produce a fourth signal; determining a ratio of the third signal and the fourth signal, wherein the ratio is indicative of the length of the multinucleotide repeat region in the target reference nucleic acid; and comparing ratio of the first signal and the second signal with the ratio of the third signal and the fourth signal. Comparison of the ratio of the first signal and the second signal with the ratio of the third signal and the fourth signal allows for detection of differences between a first nucleic acid multinucleotide repeat region, such as a sample genomic DNA containing a multinucleotide repeat region from individual subject having or is at risk of having a trinucleotide repeat expansion disorder and a reference.

Optionally, further included is amplifying a second target nucleic acid containing a second multinucleotide repeat region to produce amplified second target nucleic acids; labeling the amplified second target nucleic acids with a first label and a second label, the first label independent of the number of multinucleotide repeats and the second label proportional to the number of multinucleotide repeats; binding the amplified second target nucleic acids to a capture probe specific for the amplified second target nucleic acids; detecting the first label associated with the capture probe to produce a first signal; detecting the second label associated with the capture probe to produce a second signal; and determining a ratio of the first signal and the second signal, wherein the ratio is indicative of the length of the multinucleotide repeat in the second target nucleic acid.

Optionally, the second encoded substrate is a plurality of encoded particles, producing a second particle set.

The first and second particle sets are present together in a reaction vessel during binding of the amplified first and second target nucleic acids to the first and second encoded substrates according to some embodiments.

Methods of determining the length of a multinucleotide repeat region in a target nucleic acid which include amplifying a target nucleic acid to produce amplified target nucleic acids; labeling the amplified target nucleic acids with a first label, the first label independent of the number of multinucleotide repeats; binding the amplified target nucleic acids to a first capture probe specific for the amplified target nucleic acids; amplifying the target nucleic acid to produce multinucleotide repeat region nucleic acids; labeling the multinucleotide repeat region nucleic acids with a second label, the second label proportional to the number of multinucleotide repeats; binding the multinucleotide repeat region nucleic acids to a second capture probe specific for the multinucleotide repeat region nucleic acids; detecting the first label associated with the first capture probe to produce a first signal; detecting the second label associated with the second capture probe to produce a second signal; and determining a ratio of the first signal and the second signal, wherein the ratio is indicative of the length of the multinucleotide repeat in the target nucleic acid. Optionally, the first and second capture probes are the same. In further embodiments, the first and second capture probes are different.

Methods of screening an individual for a genetic condition characterized by an altered multinucleotide repeat region in a target nucleic acid which include amplifying from a sample obtained from the individual a target nucleic acid to produce amplified target nucleic acids, wherein the amplified target nucleic acids contain a first label, the first label independent of the number of multinucleotide repeats and the second label proportional to the number of multinucleotide repeats; binding the amplified target nucleic acids to a capture probe specific for the multinucleotide repeat of the amplified target nucleic acids; detecting the first label associated with the capture probe to produce a first signal; detecting the second label associated with the capture probe to produce a second signal; determining a ratio of the first signal to the second signal, wherein the ratio is indicative of the length of the multinucleotide repeat in the target nucleic acid, and comparing the determined ratio with that from a reference sample to determine the presence of an altered multinucleotide repeat region in the individual.

Assay compositions are provided according to embodiments described herein which include amplified target nucleic acids containing a multinucleotide repeat region, the amplified target nucleic acids including a first label and a second label, the first label independent of the number of multinucleotide repeats and the second label proportional to the number of multinucleotide repeats, wherein the first and second labels are each independently incorporated in the amplified target nucleic acids during the amplifying or after the amplifying, and wherein the amplified target nucleic acids are bound to a capture probe specific for the amplified target nucleic acids.

Figure 1A:
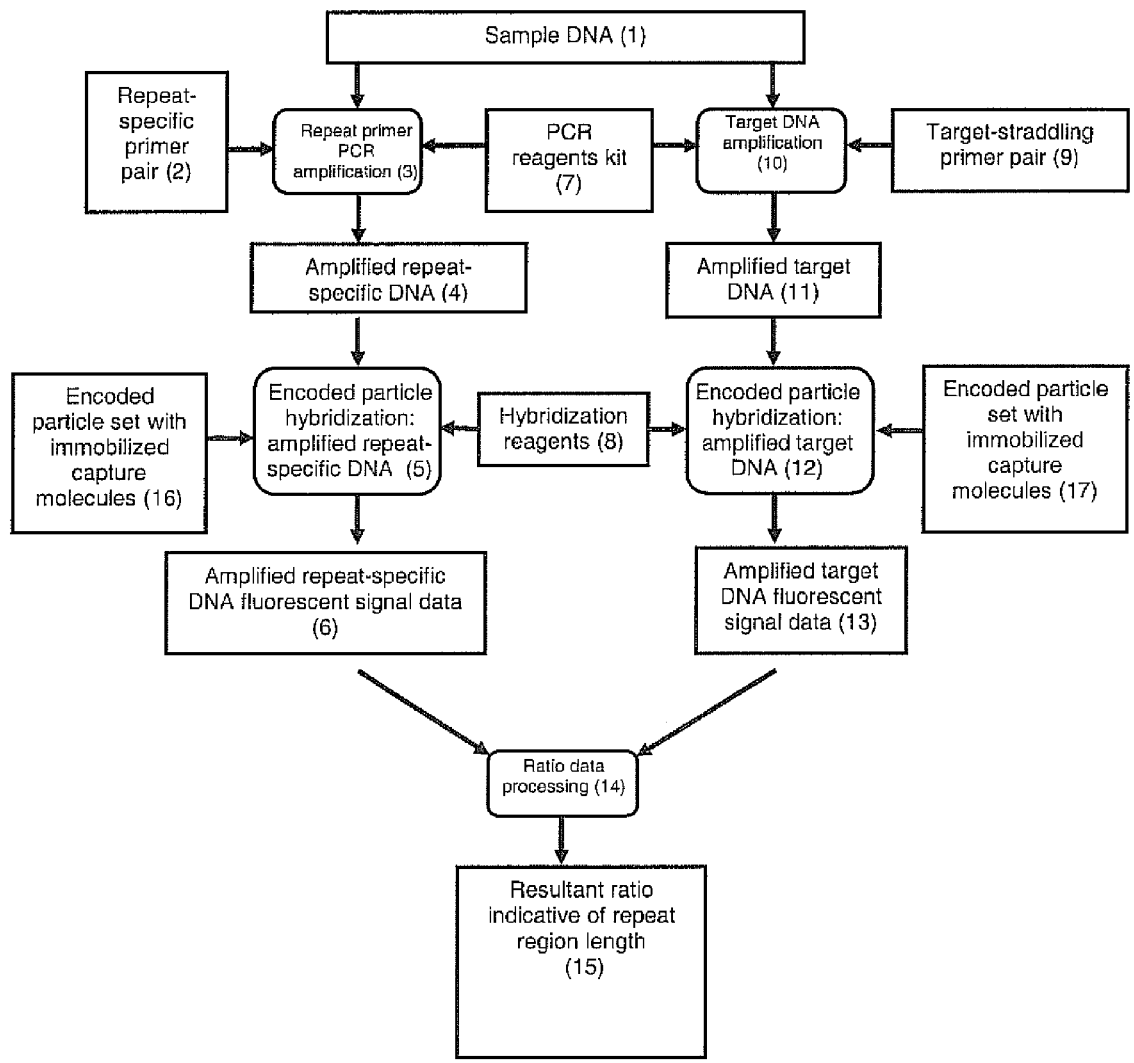
FIGS. 1A, 1B and 1C are schematic process flow charts depicting exemplary methods for determining the length of multinucleotide repeats in a target DNA molecule.

Schematic drawings provided herewith are not drawn to scale.

DETAILED DESCRIPTION OF THE INVENTION

Described herein are methods for determining the length of a multinucleotide repeat region present in a target nucleic acid.

As used herein, the term "length of a multinucleotide repeat region" means the number of multicleotide motifs, typically containing 3 or 4 nucleotides, repetitively present in a segment of target nucleic acid.

Methods of determining the length of a multinucleotide repeat region in a target nucleic acid, are provided which include amplifying a target nucleic acid to produce amplified target nucleic acids. Encoded particles which include capture probes specific for the amplified target nucleic acids are provided. The amplified target nucleic acids are then bound to encoded particles via specific binding to the capture probes. The amplified target nucleic acids are labeled with a first label and a second label. The first label is independent of the number of multinucleotide repeats and is also termed a "target-detection label" herein. The second label is proportional to the number of multinucleotide repeats and is also termed a "repeat-detection label" herein. The first label is detected to produce a first signal and the second label is detected to produce a second signal. The ratio of the first signal to the second signal is determined and the ratio is indicative of the length of the multinucleotide repeat in the target nucleic acid.

In particular embodiments, the first label, that is, the "target-detection label," is incorporated in a straddle primer used in amplifying the target nucleic acid.

In some embodiments, the second label, that is, the "repeat-detection label" is present in a repeat-specific primer used in amplifying the target nucleic acid.

In some embodiments, the "repeat-detection label" is present in nucleotides used in amplifying the target nucleic acid to produce the amplified target nucleic acids.

In some embodiments, the "repeat-detection label" is present in probes which specifically bind to multinucleotide repeats in the amplified target nucleic acids. For example, the probes which specifically bind to multinucleotide repeats in the amplified target nucleic acids are nucleic acid probes which have a complementary nucleic acid sequence according to embodiments of the present invention.

The term "nucleic acid" as used herein refers to RNA or DNA molecules having more than one nucleotide in any form including single-stranded, double-stranded, oligonucleotide or polynucleotide.

The target nucleic acid is DNA in particular embodiments and the DNA can be in any form, such as chromosomal DNA, mitochondrial DNA, cDNA, microdissected chromosomal DNA, an insert in a vector illustratively including a bacterial artificial chromosome, yeast artificial chromosome, human artificial chromosome, cosmid, plasmid, phagemid, phage DNA, and fosmid.

The target nucleic acid can be obtained from any source, including, but not limited to, a human, a non-human mammal, a vertebrate, an invertebrate, a microorganism, or a plant. The target nucleic acid can be obtained from one or more cells ex vivo or in vitro. For example, the target nucleic acid can be obtained from cultured cells, including, but not limited to, cell lines, primary cells or laboratory manipulated cells such as recombinant cells.

The target nucleic acid is typically contained within a biological sample, which can be obtained from an individual, such as from a bodily sample, for example, blood, buccal swab, skin tissue, urine, saliva, tissue, and the like, and cell lines derived therefrom. A prenatal sample can be obtained from amniotic fluid, products of conception, blastocysts and blastomeres, corionic villi, fetal cells and fetal DNA circulating in maternal blood. Archived samples extracted from formalin-fixed, paraffin-embedded (FFPE) pathology samples can be used in the methods described herein. Samples also be obtained from in vitro sources such as cell lines.

Biological samples can be obtained from any source, including, but not limited to, a human, a non-human mammal, a vertebrate, an invertebrate, a microorganism, or a plant. Biological samples can be obtained from one or more cells ex vivo or in vitro. For example, biological samples can be obtained from cultured cells, including, but not limited to, cell lines, primary cells or laboratory manipulated cells such as recombinant cells.

Target nucleic acid, such as target DNA, is obtained by methods known in the art, for instance, as described in J. Sambrook and D. W. Russell, Molecular Cloning: A Laboratory Manual, Cold Spring Harbor Laboratory Press; 3rd Ed., 2001 or F. M. Ausubel, Ed., Short Protocols in Molecular Biology, Current Protocols; 5th Ed., 2002. Target nucleic acid, such as target DNA, may also be obtained commercially and/or using commercial kits for isolation of target nucleic acid, such as target DNA.

Scientific and technical terms used herein are intended to have the meanings commonly understood by those of ordinary skill in the art. Such terms are found defined and used in context in various standard references illustratively including J. Sambrook and D. W. Russell, Molecular Cloning: A Laboratory Manual, Cold Spring Harbor Laboratory Press; 3rd Ed., 2001; F. M. Ausubel, Ed., Short Protocols in Molecular Biology, Current Protocols; 5th Ed., 2002; B. Alberts et al., Molecular Biology of the Cell, 4th Ed., Garland, 2002; D. L. Nelson and M. M. Cox, Lehninger Principles of Biochemistry, 4th Ed., W.H. Freeman & Company, 2004; and Herdewijn, P. (Ed.), Oligonucleotide Synthesis: Methods and Applications, Methods in Molecular Biology, Humana Press, 2004.

Methods for determining the length of a multinucleotide repeat region present in a target nucleic acid are useful, for example, when determining whether a disease locus, such as the Fragile X locus, contains a number of trinucleotide repeats that correlates with a disease phenotype. The presently described methods employ detectable labels that generate signals correlating with the length of a multinucleotide repeat, and thus allow determination of the length of a multinucleotide repeat region without the need for assessing the molecular weight of the repeat region or parts thereof.

Disorders associated with multinucleotide repeats include trinucleotide repeat expansion disorders such as, but not limited to Dentatorubropallidoluysian atrophy (DRPLA), Huntington's disease, spinobulbar muscular atrophy (SBMA), spinocerebellar ataxia type 1 (SCA1), spinocerebellar ataxia type 2 (SCA2), spinocerebellar ataxia type 3 (SCA3), spinocerebellar ataxia type 6 (SCA6), spinocerebellar ataxia type 7 (SCAT), spinocerebellar ataxia type 17 (SCA17), fragile X syndrome; fragile XE mental retardation; Friedreich's ataxia; myotonic dystrophy; spinocerebellar ataxia type 8 (SCA8), spinocerebellar ataxia type 12 (SCA12). All of these trinucleotide repeat expansion disorders are well-characterized. The gene affected by trinucleotide repeat expansion in each disorder is known and the location of the trinucleotide repeat expansion in each of the affected genes is well-known.

The gene involved in DRPLA is on Chromosome 12 and is designated "DRPLA." Asymptomatic individuals have about 6 to 35 copies of CAG in the DRPLA trinucleotide repeat locus. Symptomatic individuals have about 49 to 88 copies or more of the CAG repeat. The gene affected in Huntington's Disease is designated "huntingtin." Asymptomatic individuals have about 10 to 35 copies of CAG in the huntingtin trinucleotide repeat locus. Symptomatic individuals have about 40 or more copies of the CAG repeat. The gene affected in SBMA is the Androgen Receptor gene located on the X chromosome. Asymptomatic individuals have about 9 to 36 copies of CAG in the Androgen Receptor trinucleotide repeat locus. Symptomatic individuals have about 38 to 62 copies. The gene involved in SCA1 is on Chromosome 6 and is designated "SCA1." Asymptomatic individuals have about 6 to 44 copies of CAG in the SCA1 trinucleotide repeat locus. Symptomatic individuals have about 39 to 81 copies of CAG. The gene involved in SCA2 lies on Chromosome 12 and is designated "SCA2." Asymptomatic individuals have about 14 to 31 copies of CAG in the SCA2 trinucleotide repeat locus. Symptomatic individuals have about 36 to 64 copies. The gene involved in SCA3 lies on Chromosome 14 and is designated "SCA3." Asymptomatic individuals have about 12 to 43 copies of CAG in the SCA3 trinucleotide repeat locus. Symptomatic individuals have about 56 to 86 copies. The gene involved in SCA6 lies on Chromosome 19 and is designated "SCA6." Asymptomatic individuals have about 4 to 18 copies of CAG in the SCA6 trinucleotide repeat locus. Symptomatic individuals have about 21 to 33 copies. The gene involved in SCA7 lies on Chromosome 3 and is designated "SCA7." Asymptomatic individuals have about 4 to 19 copies of CAG in the SCA7 trinucleotide repeat locus. Symptomatic individuals have about 37 to 306 copies. The gene involved in SCA17 is on Chromosome 6 and is designated "SCA17." Asymptomatic individuals have about 29 to 42 copies of CAG in the SCA17 trinucleotide repeat locus. Symptomatic individuals have about 47-55 copies or more of the CAG repeat. The affected gene in Fragile X Syndrome, is designated "FMR1" which is on the X chromosome. Asymptomatic individuals have about 6 to 53 CGG repeats in the FMR1 trinucleotide repeat locus. Symptomatic individuals have about 230 repeats or more. The affected gene in Fragile XE Mental Retardation is designated "FMR2" which is on the X chromosome. Asymptomatic individuals have about 6 to 35 copies of GCC in the FMR2 trinucleotide repeat locus. Symptomatic individuals have about 200 copies or more. The affected gene in Friedreich's Ataxia is designated "X25." Asymptomatic individuals have about 7 and 34 GAA repeats in the X25 trinucleotide repeat locus. Symptomatic individuals have about 100 or more repeats. The affected gene in Myotonic Dystrophy, is designated "myotonic dystrophy protein kinase gene" (DMPK). Asymptomatic individuals have about 5 and 37 CTG repeats in the DMPK trinucleotide repeat locus. Symptomatic individuals have about 50 repeats or more. The affected gene in SCA8 is designated "SCA8." Asymptomatic individuals have about 16 to 37 repeats of CTG in the SCA8 trinucleotide repeat locus. Symptomatic individuals have about 110 to 250 repeats. The affected gene in SCA12 is designated "SCA12." Asymptomatic individuals have about 7 to 28 repeats of CAG in the SCA12 trinucleotide repeat locus. Symptomatic individuals have about 66 to 78 repeats.

Methods of screening an individual for a genetic condition characterized by an altered multinucleotide repeat region in a target nucleic acid are provided according to embodiments described herein.

The term "altered multinucleotide repeat region" refers to a multinucleotide repeat region containing a number of multinucleotide repeats which differs from a normal number of multinucleotide repeats in the multinucleotide repeat region. An altered multinucleotide repeat region can be detected using a normal multinucleotide repeat region as a reference in embodiments of methods described herein. Thus, according to embodiments of methods described herein, a target nucleic acid which is a "reference" sample, that is, a target nucleic acid having a known number of multinucleotide repeats, is included.

An altered multinucleotide repeat region can be detected by comparison of the number of multinucleotide repeats detected using methods described herein with known number of multinucleotide repeats present in the normal multinucleotide repeat region. The term "normal" refers to the predominate number of multinucleotide repeats present in the particular analog multinucleotide repeat region found in healthy subjects.

Methods of screening an individual for a genetic condition characterized by an altered multinucleotide repeat region in a target nucleic acid include amplifying a target nucleic acid from a sample obtained from the individual to produce amplified target nucleic acids containing a first label, the first label independent of the number of multinucleotide repeats in the target nucleic acid and a second label, the second label proportional to the number of multinucleotide repeats in the target nucleic acid. The amplified target nucleic acids are bound to a capture probe specific for the multinucleotide repeat of the amplified target nucleic acids. The first label associated with the capture probe is detected to produce a first signal and the second label associated with the capture probe is detected to produce a second signal. A ratio of the first signal to the second signal is determined wherein the ratio is indicative of the length of the multinucleotide repeat in the target nucleic acid. The determined ratio relating to the sample from the individual is compared with a reference. According to embodiments of described methods, the reference is a control sample of nucleic acids obtained from a normal individual.

Methods of screening an individual for a genetic condition characterized by an altered multinucleotide repeat region in a target genomic locus containing a multinucleotide repeat region include amplifying a target genomic locus containing a multinucleotide repeat region from a sample obtained from the individual to produce amplified target genomic DNA containing a first label, the first label independent of the number of multinucleotide repeats in the target genomic DNA and a second label, the second label proportional to the number of multinucleotide repeats in the target genomic DNA. The amplified target genomic DNA is bound to capture probes specific for the multinucleotide repeat of the amplified target genomic DNA. The first label associated with the capture probe is detected to produce a first signal and the second label associated with the capture probe is detected to produce a second signal. A ratio of the first signal to the second signal is determined wherein the ratio is indicative of the length of the multinucleotide repeat in the target genomic locus. The determined ratio relating to the sample from the individual is compared with a reference. According to embodiments of described methods, the reference is a control sample of genomic DNA obtained from a normal individual.

Labels

As described herein, the amplified target nucleic acids are labeled with a first label, the "target-detection label" and a second label, the "repeat-detection label."

The target-detection label is independent of the number of multinucleotide repeats in the multinucleotide repeat region of the target nucleic acid. Any number of target-detection labels can be incorporated into the amplified target nucleic acids as long as the number of target-detection labels incorporated does not vary significantly among the individual amplified nucleic acid molecules. According to embodiments described herein, each amplified nucleic acid molecule contains a label incorporated in at least one primer of a primer pair used in amplifying the target nucleic acids to produce the amplified target nucleic acids.

Thus, in particular embodiments, the "target-detection label," is incorporated in at least one straddle primer of a straddle primer pair used in amplifying the target nucleic acid. Optionally, both primers of a straddle primer pair used in amplifying the target nucleic acid are labeled.

The repeat-detection label" is proportional to the number of multinucleotide repeats in the multinucleotide repeat region of the target nucleic acid.

In some embodiments, the "repeat-detection label" is present in a repeat-specific primer used in amplifying the target nucleic acid.

In some embodiments, the "repeat-detection label" is present in nucleotides used in amplifying the target nucleic acid to produce the amplified target nucleic acids.

In some embodiments, the "repeat-detection label" is present in probes which specifically bind to multinucleotide repeats in the amplified target nucleic acids. For example, the probes which specifically bind to multinucleotide repeats in the amplified target nucleic acids are nucleic acid probes which have a complementary nucleic acid sequence according to embodiments of the present invention.

The term "label" refers to a substance that can be measured and/or observed, visually or by any appropriate direct or indirect method illustratively including, but not limited to, spectroscopic, optical, photochemical, biochemical, enzymatic, electrical and/or immunochemical methods of detection, to indicate presence of the label. Non-limiting examples of labels that can be used in conjunction with methods described herein illustratively include a fluorescent moiety, a chemiluminescent moiety, a bioluminescent moiety, a magnetic particle, an enzyme, a substrate, a radioisotope and a chromophore.

For example, nucleotides, nucleotide analogs and/or primers can be labeled with a dye, such as a fluorophore, a chromophore, a radioactive moiety or a member of a specific binding pair such as biotin. The term "member of a specific binding pair" refers to a substance that specifically recognizes and interacts with a second substance exemplified by specific binding pairs such as biotin-avidin, biotin-streptavidin, antibody-antigen, and target-aptamer. Non-limiting examples of labels that can be used include fluorescent dyes such as fluorescein, fluorescein isothiocyanate, rhodamine, rhodamine isothiocyanate, Texas Red, cyanine dyes such as Cyanine 3 and Cyanine 5, and ALEXA dyes; chromophores such as horseradish peroxidase, alkaline phosphatase and digoxigenin; and radioactive moieties such as 32P, 35S, 3H, 125I or 14C; and binding partners such as biotin and biotin derivatives. Methods for detectably labeling nucleotides, nucleotide analogs and/or primers are well-known in the art.

Nucleotides, including, but not limited to, deoxynucleotide triphosphates (dNTPs) and analogs thereof, labeled or unlabeled, can be included in primers and/or amplification reaction mixtures according to methods described herein. The term "nucleotide analog" in this context refers to a modified or non-naturally occurring nucleotide, particularly nucleotide analogs which can be polymerized, with naturally occurring nucleotides or non-naturally occurring nucleotides, by template directed nucleic acid amplification catalyzed by a nucleic acid polymerase. Nucleotide analogs are well-known in the art. Particular nucleotide analogs are capable of Watson-Crick pairing via hydrogen bonds with a complementary nucleotide and illustratively include, but are not limited to, those containing an analog of a nucleotide base such as substituted purines or pyrimidines, deazapurines, methylpurines, methylpyrimidines, aminopurines, aminopyrimidines, thiopurines, thiopyrimidines, indoles, pyrroles, 7-deazaguanine, 7-deazaadenine, 7-methylguanine, hypoxanthine, pseudocytosine, pseudoisocytosine, isocytosine, isoguanine, 2-thiopyrimidines, 4-thiothymine, 6-thioguanine, nitropyrrole, nitroindole, and 4-methylindole. Nucleotide analogs include those containing an analog of a deoxyribose such as a substituted deoxyribose, a substituted or non-substituted arabinose, a substituted or non-substituted xylose, and a substituted or non-substituted pyranose. Nucleotide analogs include those containing an analog of a phosphate ester such as phosphorothioates, phosphorodithioates, phosphoroamidates, phosphoroselenoates, phosophoroanilothioates, phosphoroanilidates, phosphoroamidates, boronophosphates, phosphotriesters, and alkylphosphonates such as methylphosphonates.

Capture Probes

Capture probe specific for the amplified nucleic acid are present on a solid or semi-solid substrate for attachment of the amplified nucleic acid to the substrate. Capture probes can be in any form which allows for attachment to the substrate and specific capture of the amplified nucleic acid.

According to some embodiments, capture probes are nucleic acids which include a nucleic acid sequence complementary to the amplified target nucleic acids. Capture probes attached to a substrate can be single-stranded and/or double-stranded nucleic acids. In particular embodiments, where double-stranded nucleic acids capture probes are bound to the substrate, they are denatured and rendered single stranded after immobilization to the substrate for preparation for use in certain embodiments of assay methods. Optionally, double stranded nucleic acid probes are denatured prior to immobilization and the single stranded nucleic acids are then bound to the substrate.

The term "complementary" as used herein refers to Watson-Crick base pairing between nucleotides and specifically refers to nucleotides hydrogen bonded to one another with thymine or uracil residues linked to adenine residues by two hydrogen bonds and cytosine and guanine residues linked by three hydrogen bonds. In general, a nucleic acid includes a nucleotide sequence described as having a "percent complementarity" to a specified second nucleotide sequence. For example, a nucleotide sequence may have 80%, 90%, or 100% complementarity to a specified second nucleotide sequence, indicating that 8 of 10, 9 of 10 or 10 of 10 nucleotides of a sequence are complementary to the specified second nucleotide sequence. For instance, the nucleotide sequence 3'-TCGA-5' is 100% complementary to the nucleotide sequence 5'-AGCT-3'. Further, the nucleotide sequence 3'-TCGA- is 100%, or completely, complementary to a region of the nucleotide sequence 5'-TTAGCTGG-3'. Determination of particular hybridization conditions relating to a specified nucleic acid is routine and is well known in the art, for instance, as described in J. Sambrook and D. W. Russell, Molecular Cloning: A Laboratory Manual, Cold Spring Harbor Laboratory Press; 3rd Ed., 2001; and F. M. Ausubel, Ed., Short Protocols in Molecular Biology, Current Protocols; 5th Ed., 2002. High stringency hybridization conditions are those which only allow hybridization of substantially complementary nucleic acids. Typically, nucleic acids having about 85-100% complementarity are considered highly complementary and hybridize under high stringency conditions. Intermediate stringency conditions are exemplified by conditions under which nucleic acids having intermediate complementarity, about 50-84% complementarity, as well as those having a high degree of complementarity, hybridize. In contrast, low stringency hybridization conditions are those in which nucleic acids having a low degree of complementarity hybridize. The terms "specific hybridization" and "specifically hybridizes" refer to hybridization of a particular nucleic acid to a complementary nucleic acid without substantial hybridization to nucleic acids other than the complementary nucleic acid in a sample.

Substrates

A solid substrate, which includes semi-solid substrate, for attachment of a capture probe can be any of various materials such as glass; plastic, such as polypropylene, polystyrene, nylon; paper; silicon; nitrocellulose; or any other material to which a nucleic acid can be attached for use in an assay. The substrate can be in any of various forms or shapes, including planar, such as silicon chips and glass plates; and three-dimensional, such as particles, microtiter plates, microtiter wells, pins, fibers and the like.

A substrate to which a capture probe is attached is encoded according to embodiments of methods and compositions of the present invention. Encoded substrates are distinguishable from each other based on a characteristic illustratively including an optical property such as color, reflective index and/or an imprinted or otherwise optically detectable pattern. For example, the substrates can be encoded using optical, chemical, physical, or electronic tags.

In particular aspects, a solid substrate to which a capture probe is attached is a particle.

Particles to which a capture probe is attached can be any solid or semi-solid particles which are stable and insoluble in use, such as under hybridization and label detection conditions. The particles can be of any shape, such as cylindrical, spherical, and so forth; size, such as microparticles and nanoparticles; composition; and have various physiochemical characteristics. The particle size or composition can be chosen so that the particle can be separated from fluid, e.g., on a filter with a particular pore size or by some other physical property, e.g., a magnetic property.

Microparticles, such as microbeads, used can have a diameter of less than one millimeter, for example, a size ranging from about 0.1 to about 1,000 micrometers in diameter, inclusive, such as about 3-25 microns in diameter, inclusive, or about 5-10 microns in diameter, inclusive. Nanoparticles, such as nanobeads used can have a diameter from about 1 nanometer (nm) to about 100,000 nm in diameter, inclusive, for example, a size ranging from about 10-1,000 nm, inclusive, or for example, a size ranging from 200-500 nm, inclusive. In certain embodiments, particles used are beads, particularly microbeads and nanobeads.

Particles are illustratively organic or inorganic particles, such as glass or metal and can be particles of a synthetic or naturally occurring polymer, such as polystyrene, polycarbonate, silicon, nylon, cellulose, agarose, dextran, and polyacrylamide. Particles are latex beads in particular embodiments.

Particles used include functional groups for attaching nucleic acid capture probes in particular embodiments. For example, particles can include carboxyl, amine, amino, carboxylate, halide, ester, alcohol, carbamide, aldehyde, chloromethyl, sulfur oxide, nitrogen oxide, epoxy and/or tosyl functional groups. Functional groups of particles, modification thereof and binding of a chemical moiety, such as a nucleic acid, thereto are known in the art, for example as described in Fitch, R. M., Polymer Colloids: A Comprehensive Introduction, Academic Press, 1997. U.S. Pat. No. 6,048,695 describes an exemplary method for attaching nucleic acid capture probes to a substrate, such as particles. In a further particular example, 1-Ethyl-3-[3-dimethylaminopropyl]carbodiimide hydrochloride, EDC or EDAC chemistry, can be used to attach nucleic acid capture probes to particles.

Particles to which a capture probe is attached are encoded particles according to embodiments of methods and compositions of the present invention. Encoded particles are particles which are distinguishable from other particles based on a characteristic illustratively including an optical property such as color, reflective index and/or an imprinted or otherwise optically detectable pattern. For example, the particles may be encoded using optical, chemical, physical, or electronic tags. Encoded particles can contain or be attached to, one or more fluorophores which are distinguishable, for instance, by excitation and/or emission wavelength, emission intensity, excited state lifetime or a combination of these or other optical characteristics. Optical bar codes can be used to encode particles.

In particular embodiments, the code is embedded, for example, within the interior of the particle, or otherwise attached to the particle in a manner that is stable through hybridization and analysis. The code can be provided by any detectable means, such as by holographic encoding, by a fluorescence property, color, shape, size, light emission, quantum dot emission and the like to identify particle and thus the capture probes immobilized thereto. In some embodiments, the code is other than one provided by a nucleic acid.

One exemplary platform utilizes mixtures of fluorescent dyes impregnated into polymer particles as the means to identify each member of a particle set to which a specific capture probe has been immobilized. Another exemplary platform uses holographic barcodes to identify cylindrical glass particles. For example, Chandler et al. (U.S. Pat. No. 5,981,180) describes a particle-based system in which different particle types are encoded by mixtures of various proportions of two or more fluorescent dyes impregnated into polymer particles. Soini (U.S. Pat. No. 5,028,545) describes a particle-based multiplexed assay system that employs time-resolved fluorescence for particle identification. Fulwyler (U.S. Pat. No. 4,499,052) describes an exemplary method for using particle distinguished by color and/or size. U.S. Patent Application Publications 20040179267, 20040132205, 20040130786, 20040130761, 20040126875, 20040125424, and 20040075907 describe exemplary particles encoded by holographic barcodes. U.S. Pat. No. 6,916,661 describes polymeric microparticles that are associated with nanoparticles that have dyes that provide a code for the particles While an embodiment described in detail herein utilizes the Luminex encoded bead platform, other types of encoded particle assay platforms may be used, such as the VeraCode beads and BeadXpress system (Illumina Inc., San Diego Calif.), xMAP 3D (Luminex) and the like. Magnetic Luminex beads can be used which allow wash steps to be performed with plate magnets and pipetting rather than with filter plates and a vacuum manifold. Each of these platforms are typically provided as carboxyl beads but may also be configured to include a different coupling chemistry, such as amino-silane.

Particles are typically evaluated individually to detect encoding. For example, the particles can be passed through a flow cytometer. Exemplary flow cytometers include the Coulter Elite-ESP flow cytometer, or FACScan™ flow cytometer available from Beckman Coulter, Inc. (Fullerton Calif.) and the MOFLO™ flow cytometer available from Cytomation, Inc., Fort Collins, Colo. In addition to flow cytometry, a centrifuge may be used as the instrument to separate and classify the particles. A suitable system is that described in U.S. Pat. No. 5,926,387. In addition to flow cytometry and centrifugation, a free-flow electrophoresis apparatus may be used as the instrument to separate and classify the particles. A suitable system is that described in U.S. Pat. No. 4,310,408. The particles may also be placed on a surface and scanned or imaged.

Provided are assays according to embodiments of the present invention using more than one type of encoded particles. In particular embodiments, a "particle set" is provided wherein each particle of the particle set is encoded with the same code such that each particle of a particle set is distinguishable from each particle of another "particle set." In further embodiments, two or more codes can be used for a single particle set. Each particle can include a unique code, for example. In certain embodiments, particle encoding includes a code other than or in addition to, association of a particle and a nucleic acid capture probe specific for a target nucleic acid.

Methods including two or more particle sets can be used in multiplex or separate assay formats.

Binding of Capture Probes to Substrate

Binding of the nucleic acid capture probes to a substrate is achieved by any of various methods effective to bond a nucleic acid to a solid or semi-solid substrate, illustratively including adsorption and chemical bonding. The nucleic acids can be bonded directly to the material of the encoded particles or indirectly bonded to the encoded particles, for example, via bonding to a coating or linker disposed on the particles. Nucleic acids can be synthesized, and/or modified once synthesized, to include a functional group for use in bonding the nucleic acids to particles. For example, the nucleic acids sequences used as probes can include carboxyl, amine, amino, carboxylate, halide, ester, alcohol, carbamide, aldehyde, chloromethyl, sulfur oxide, nitrogen oxide, epoxy and/or tosyl functional groups.

In particular embodiments of assays described herein, amplified target nucleic acids are captured by the capture probes attached to the encoded particles by hybridization.

The terms "hybridization" and "hybridized" refer to pairing and binding of complementary nucleic acids. Hybridization occurs to varying extents between two nucleic acids depending on factors such as the degree of complementarity of the nucleic acids, the melting temperature, Tm, of the nucleic acids and the stringency of hybridization conditions, as is well known in the art. The term "stringency of hybridization conditions" refers to conditions of temperature, ionic strength, and composition of a hybridization medium with respect to particular common additives such as formamide and Denhardt's solution.

Amplification

Amplification of a target nucleic acid is achieved using an in vitro amplification method. The term "amplification method" refers to a method for copying a template target nucleic acid, thereby producing nucleic acids which include copies of all or a portion of the template target nucleic acid.

Amplification methods included in embodiments of the present invention are those which include template directed primer extension catalyzed by a nucleic acid polymerase using a pair of primers which flank the target nucleic acid, illustratively including, but not limited to, Polymerase Chain Reaction (PCR), reverse-transcription PCR (RT-PCR), ligation-mediated PCR (LM-PCR), phi-29 PCR, and other nucleic acid amplification methods, for instance, as described in C. W. Dieffenbach et al., PCR Primer: A Laboratory Manual, Cold Spring Harbor Laboratory Press, 2003; and V. Demidov et al., DNA Amplification: Current Technologies and Applications, Taylor & Francis, 2004.

The terms "amplified nucleic acid" and "amplified DNA" as well as plurals thereof refer to the product of a process of copying a target nucleic acid template.

Primers

The term "primer" refers to an oligonucleotide nucleic acid that is capable of acting as a site of initiation of synthesis of a template directed primer extension product under appropriate reaction conditions. An oligonucleotide primer is typically about 10-30 contiguous nucleotides in length and may be longer or shorter. An oligonucleotide primer is completely or substantially complementary to a region of a template nucleic acid such that, under hybridization conditions, the oligonucleotide primer anneals to the complementary region of the template nucleic acid. Appropriate reactions conditions for synthesis of a primer extension product include presence of suitable reaction components including, but not limited to, a polymerase and nucleotide triphosphates. Design of oligonucleotide primers suitable for use in amplification reactions is well known in the art, for instance as described in A. Yuryev et al., PCR Primer Design, Humana Press, 2007.

Primer design for amplification of a target nucleic acid is well-known to those of skill in the art. Primers for amplification of a target nucleic acid are designed according to well-known methods and criteria. For instance, the annealing temperature of the primers should be about the same, within a few degrees, the primers should not form dimers with each other and the primers should not form secondary structures, such as hairpins. Methods and considerations for primer design and amplification procedures are described in detail in Yuryev, A., PCR Primer Design, Methods in Molecular Biology, vol. 42, Human Press, 2007; C. W. Dieffenbach et al., PCR Primer: A Laboratory Manual, Cold Spring Harbor Laboratory Press, 2003; and V. Demidov et al., DNA Amplification: Current Technologies and Applications, Taylor & Francis, 2004.

Amplified nucleic acids optionally contain additional materials such as, but not limited to, nucleic acid sequences, functional groups for chemical reaction and detectable labels, present in the primers and not present in the original DNA template. Such primer-derived materials add functionality such as primer binding sites for additional amplification reactions and/or a functional group for chemical bonding to a substrate.

In embodiments of the present invention a pair of primers used in amplification includes primers which flank a multi-nucleotide repeat region, that is, one of the primers has a nucleotide sequence complementary to a region of the target nucleic acid upstream of the multinucleotide repeat region and a second primer of the primer pair has a nucleotide sequence complementary to a region of the target nucleic acid downstream of the multinucleotide repeat region. Such primers are termed "straddle primers" herein. Numerous straddle primer pairs designed to amplify a target nucleic acid containing a multinucleotide repeat and which flank the multinucleotide repeat region are known in the art, any of which can be used in conjunction with methods and compositions of the present invention. Alternatively, straddle primers can be designed and used with only routine experimentation.

Exemplary straddle primers and their use to amplify a target nucleic acid including a multinucleotide repeat region are described in Examples detailed herein.

Straddle primers to amplify a target nucleic acid including a multinucleotide repeat region present in the FMR1 gene are described in Wilson, J A et al., J. Molec. Diagnostics, 10(1): 2-12, 2008 and include: 1) Forward primer 5'-GGAA-CAGCGTTGATCACGTGACGTGGTTTC-3'-(SEQ ID No. 1); reverse primer 5'-GGGGCCTGCCCTAGAGCCAAG-TACCTTGT-3' (SEQ ID No. 2) (Chong, S S. et al., Am. J. Med. Genet., 1994, 51:522-526); 2) Forward primer 5'-GACGGAGGCGCCCGTGCCAGG-3' (SEQ ID No. 3); reverse primer 5'-TCCTCCATCTTCTCTTCAGCCCT-3' (SEQ ID No. 4) (Pergolizzi, R G. et al., Lancet, 1992, 339: 271-272); 3) Forward primer 5'-TGACGGAGGCGCCGCT-GCCAGGGGGCGTGC-3' (SEQ ID No. 5); reverse primer 5'-GAGAGGTGGGCTGCGGGCGCTCGAGGCCCA-3' (SEQ ID No. 6) (Wang Q., et al., J. Med Genet., 1995, 32:170-173); 4) Forward primer 5'-AGGCGCTCAGCTC-CGTTTCGGTTTCACTTC-3' (SEQ ID No. 7); reverse primer 5'-GTGGGCTGCGGGCGCTCGAGG-3' (SEQ ID No. 8) (Tarlton, J., Neurogenetics: Methods and Protocols (Methods in Molecular Biology, v. 217, Potter, N., Ed., Humana Press Inc., Totowa, N.J., 2003), pp 29-39); 5) Forward primer 5'-GCTCAGCTCCGTTTCGGTTTCACTTC-CGGT-3' (SEQ ID No. 9); reverse primer 5'-AGCCCCG-CACTTCCACCACCAGCTCCTCCA-3' (SEQ ID No. 10) (Verkerk, A J. et al., Cell, 1991, 65:905-914; Fu, Y H et al., Cell, 1991, 67:1047-1058); 6) Forward primer 5'-GACG-GAGGCGCCGCTGCCAGG-3' (SEQ ID No. 11); reverse primer 5'-GTGGGCTGCGGGCGCTCGAGG-3' (SEQ ID No. 12) (Verkerk, A J. et al., Cell, 1991, 65:905-914); and 7) Forward primer 5'-GTGACGGAGGCGCCGCTGCCA-3' (SEQ ID No. 13); reverse primer 5'-AGCTCCTCCATCT-TCTCTTCAGCCCTGCTA-3'(SEQ ID No. 14) (Fu, Y H et al., Cell, 1991, 67:1047-1058.)

In embodiments of the present invention a pair of primers used in amplification includes a straddle primer and a repeat-specific primer. The straddle primer has a nucleotide sequence complementary to a region of the target nucleic acid upstream of the multinucleotide repeat region or complementary to a region of the target nucleic acid downstream of the multinucleotide repeat region. The repeat-specific primer has a nucleotide sequence complementary to a portion of the multinucleotide repeat region of the target nucleic acid. Exemplary primer pairs including a straddle primer and a repeat-specific primer are described herein. Alternatively, such primers can be designed and used with only routine experimentation.

In one embodiment, the method involves amplifying the target nucleic acid molecule using a target-straddling primer pair, wherein one primer contains a target-detection label; hybridizing the amplified target DNA molecule to a set of encoded particles, the particles comprising a capture molecule selective for the amplified target nucleic acid molecule; detecting a signal produced by the target-detection label; amplifying segments of the multinucleotide repeat region using a repeat-specific primer pair, wherein one primer of the repeat-specific primer pair is specific for the multinucleotide repeat motif, and the other primer of the repeat-specific primer pair is specific for a target nucleic acid molecule sequence outside of the multinucleotide repeat region and contains a repeat-detection label, to produce amplified repeat-specific nucleic acid molecules; and hybridizing the amplified repeat-specific nucleic acid molecules to a set of encoded particles, the particles comprising a capture molecule selective for the amplified repeat-specific nucleic acid molecules; detecting a signal produced by the repeat-detection label; determining a ratio of signals produced by the target-detection label and repeat-detection label; determining the length of the multinucleotide repeat region based on the determined ratio.

As is described herein below, also hybridized to the amplified target DNA molecules are one or more repeat-detector probes, which contain a repeat-detection label. The repeat-detector probe molecules are complementary to the repeat region (i.e. the multinucleotide repeat motif) and thus a plurality of repeat-detector probes can hybridize to the repeat region. The repeat-detector probes can be hybridized with the amplified target DNA molecules together with or after the amplified target DNA molecules have been captured by the particles.

In another embodiment, the method for determining the length of a multinucleotide repeat region present in a target nucleic acid molecule involves amplifying the target nucleic acid molecule using a target-straddling primer pair, wherein one primer contains a target-detection label; hybridizing a first portion of the amplified target nucleic acid molecules to a first set of encoded particles, the particles including a capture molecule selective for the amplified target nucleic acid molecules; detecting a signal produced by the target-detection label; hybridizing a second portion of the amplified target nucleic acid molecules with a detectable probe specific for the multinucleotide repeat motif and a second set of encoded particles, the particles including a capture molecule selective for the amplified target DNA molecules; detecting a signal produced by the probe (i.e., the repeat-detection probe containing the repeat-detection label); determining a ratio of signals produced by the target-detection label and probe; and determining the length of the multinucleotide repeat region based on the determined ratio.

In a further embodiment, the method for determining the length of a multinucleotide repeat region present in a target nucleic acid molecule involves amplifying the target nucleic acid molecule using a target-straddling primer pair, wherein one primer contains a target-detection label, in the presence of at least one type of deoxynucleotide comprising a repeat-detection label; hybridizing the amplified target nucleic acid molecule to a set of encoded particles, the particles comprising a capture molecule selective for the amplified target nucleic acid molecule, and detecting a signal produced by the target-detection label. The method can further include detecting a signal produced by the repeat-detection label; determining a ratio of signals produced by the target-detection label and repeat-detection label; and determining the length of the multinucleotide repeat region based on the determined ratio. There is a repeat-detection label on a detectable probe specific for the multinucleotide repeat motif.

In an embodiment, the method involves amplifying the target nucleic acid molecule using a target-straddling primer pair, in the presence of deoxynucleotide comprising a repeat-detection label, wherein a primer of the pair contains a target-detection label, binding the amplified target DNA molecule to a set of encoded particles, each particle comprising a binding element selective for the multinucleotide repeat of the amplified target nucleic acid molecule; detecting a signal corresponding to an amount of the target-detection label present in amplified target nucleic acid molecules that are particle-bound; detecting a signal corresponding to an amount of the repeat-detection label present in amplified target nucleic acid molecules bound to the particles; determining a ratio of signals from the target-detection label and repeat-detection label; and determining the length of the multinucleotide repeat region based on the determined ratio.

Figure 11:
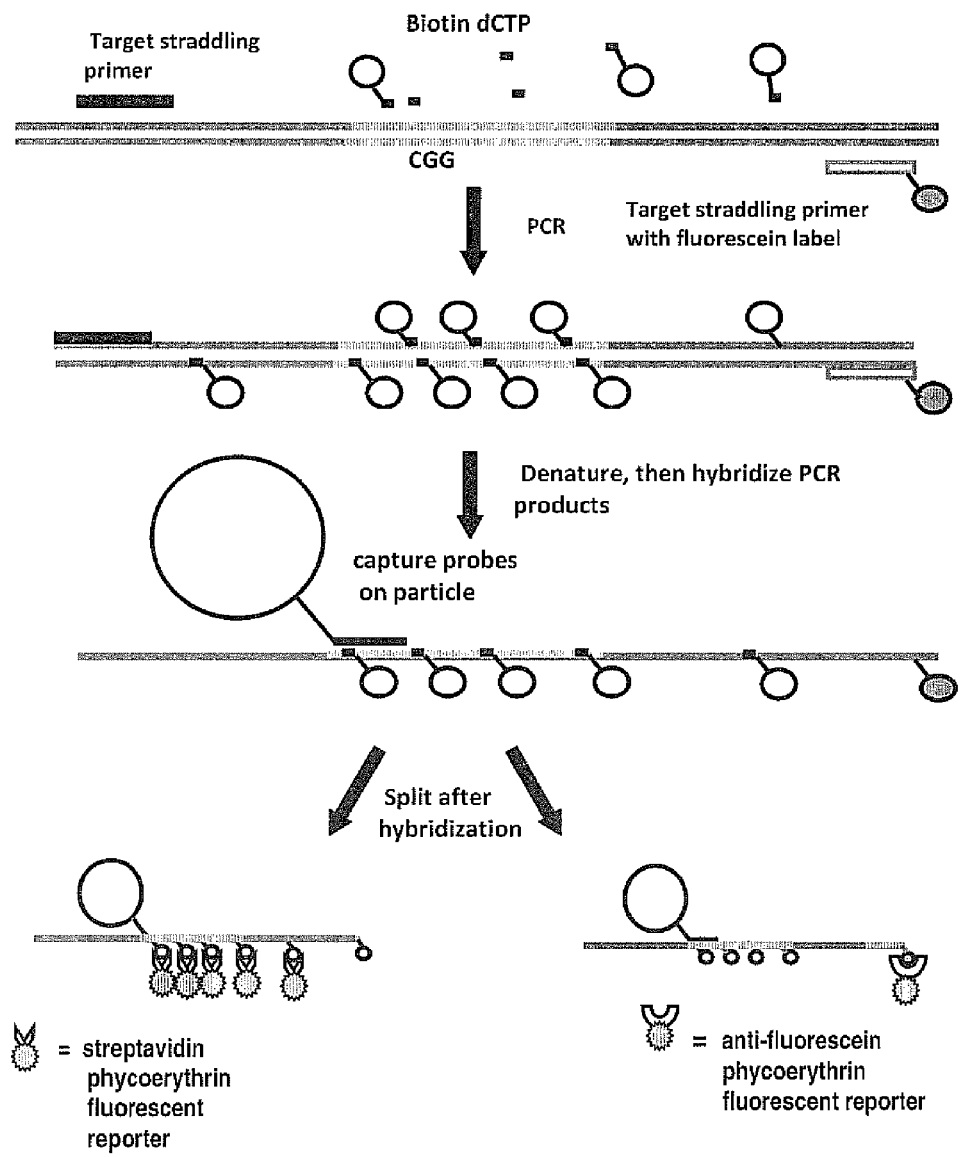
FIG. 11 is a schematic drawing depicting an exemplary method for determining the length of a multinucleotide repeat region present in a target DNA molecule.

In another embodiment, the method involves amplifying the target nucleic acid molecule using a target-straddling primer pair, in the presence of deoxynucleotide comprising a repeat-detection label, wherein a primer of the pair contains a target-detection label, binding the amplified target DNA molecule to a set of encoded particles, each particle comprising a binding element selective for the amplified target nucleic acid molecule; contacting a portion of the particle-bound amplified target nucleic acid with a reporter that renders detectable the target-detection label; detecting a signal corresponding to an amount of the target-detection label present in amplified target nucleic acid molecules that are particle-bound; contacting another portion of the particle-bound amplified target nucleic acid molecules with a reporter that renders detectable the repeat-detection label; detecting a signal corresponding to an amount of the repeat-detection label present in amplified target nucleic acid molecules bound to the particles; determining a ratio of signals from the target-detection label and repeat-detection label; and determining the length of the multinucleotide repeat region based on the determined ratio. An exemplary implementation of this method is illustrated in FIG. 11. In this specific example, the binding element selective for the amplified target nucleic acid molecule is present in the multinucleotide repeat region. Other portions of an amplified target nucleic acid molecule also can be used.

Figure 1B:
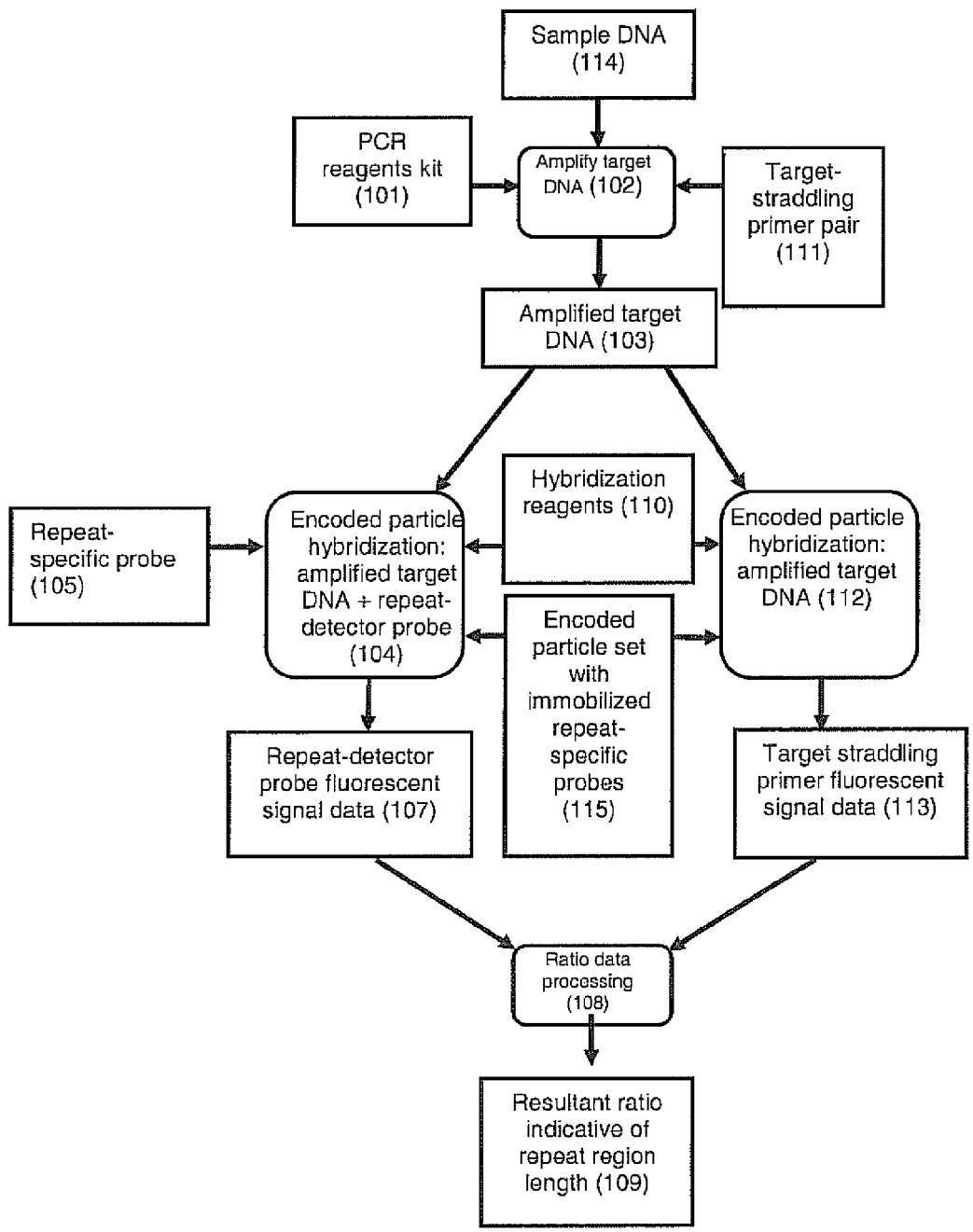

Methods described herein involve using encoded particles for determining the length of a multinucleotide repeat region present in a target nucleic acid molecule. In an embodiment, the determination is based on both the number or relative amount of amplified target nucleic acid molecules and the number or relative amount of multinucleotide repeats within the amplified nucleic acid molecule. The number or relative amount of amplified target nucleic acid molecules and the number of multinucleotide repeats can be determined using separate pools of amplified nucleic acid as is illustrated in FIG. 1A, or can be determined from a common pool of amplified target nucleic acid, as is illustrated in FIGS. 1B and 11. The methods can proceed using various strategies, which can be selected by the user based, for example, on assay format and detectable label preferences or requirements imposed by available instrumentation.

Figure 13:
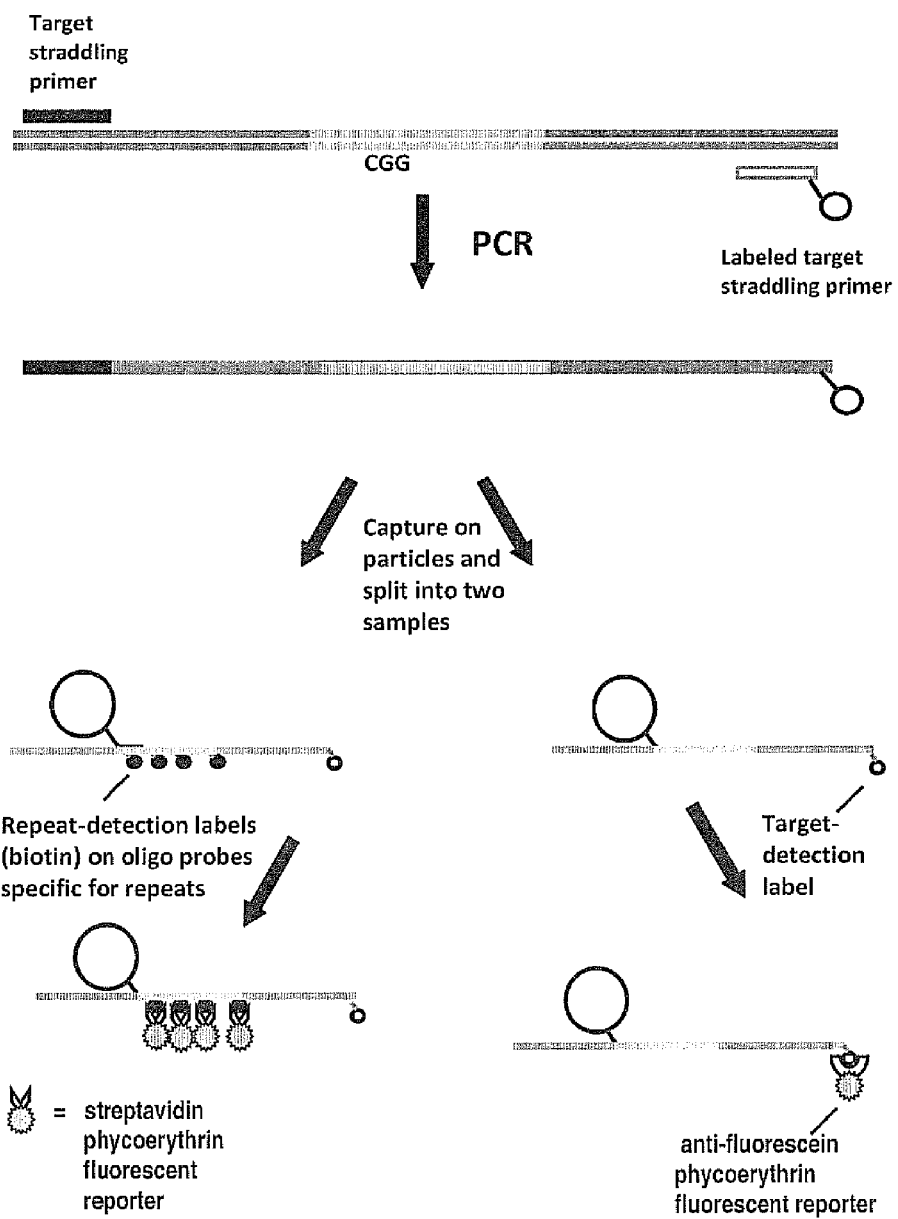
FIG. 13 is a schematic drawing depicting an exemplary method for determining the length of a multinucleotide repeat region present in a target DNA molecule.

FIG. 13 illustrates an embodiments of methods described herein in which a target nucleic acid containing a multinucleotide repeat region (labeled "CGG repeats" is amplified using a pair of straddle primers, wherein one of the pair has a target detection label. In this case the target detection label is a fluorescein label. Following amplification, the target detection label is incorporated into the amplified nucleic acids, as illustrated.

The amplified nucleic acids are bound to encoded particles via hybridization with complementary nucleic acid capture probes and the resulting particle set is split into two portions.

A first portion is bound to repeat detection probes, in this case by specific hybridization to labeled oligonucleotides having a sequence complementary to a portion of the multinucleotide repeat region. Biotin labeled oligonucleotides in this case are the repeat-detection label. A streptavidin reporter is used to detect the label and generate a first signal.

A second portion is bound to a reporter specific for the target detection label fluorescein, in this casean anti-fluorescein antibody, and generate a second signal.

The signal from the repeat detection label is compared to the signal detected from the target detection label to determine the length of the multinucleotide repeat region.

Methods described herein involve amplifying DNA molecules. The amplification can be performed using any suitable polynucleotide amplification technique. Polymerase chain reaction is described herein, and other published amplification methods can be adapted for use with the methods described herein.

Methods described herein involve detection of labels. Any of a variety of labels and their complementary detection modes can be used when practicing the described methods. The Examples below describe use of the fluorescent label phycoerythrin in conjunction with a fluorescence reader of a Luminex 200 instrument, although other assay reading platforms such as the Illumina BeadExpress, microplates, microarrays, etc. could be used with their appropriate labels. Platforms that utilize 2 or more labels could accomplish the assay without the need for splitting the intermediate assay product into two vessels prior to reading, as the single-label Luminex examples incorporated herein require.

Any appropriate method, illustratively including spectroscopic, optical, photochemical, biochemical, enzymatic, electrical and/or immunochemical is used to detect a label in an assay described herein. The ratio of the first signal to the second signal can be determined by manual, machine or automated methods and the resulting ratio is indicative of the length of the multinucleotide repeat in the target nucleic acid.

A method of assaying sample nucleic acid is provided which includes two or more encoded particle sets encoded such that each particle of each encoded particle set is detectably distinguishable from each particle of each other encoded particle set. The encoded particles of a first particle set include attached capture probes which specifically capture amplified target nucleic acids corresponding to a first target nucleic acid containing a multinucleotide repeat region. The encoded particles of a second particle set include attached capture probes which specifically capture amplified target nucleic acids corresponding to a second target nucleic acid containing a multinucleotide repeat region.

Methods described can be performed in any suitable container. In particular embodiments, for example, where multiple samples are to be assayed, a multi-chamber container can be used. Multi-chamber containers illustratively include multi-depression substrates such as slides, silicon chips or trays. In some embodiments, each sample is disposed in a different well of a multi-well plate. For example, a multi-well plate can be a 96-well, 384-well, 864-well or 1536-well assay plate.

Kits for determining the length of multinucleotide repeats in a target nucleic acid are provided. In particular embodiments, a kit is provided which includes an encoded particle set and/or a mixture of two or more encoded particle sets, wherein each particle set includes attached capture probes specific for a target nucleic acid. Instructional material for use of the encoded particle set and/or multiplex reagent including two or more encoded particle sets is optionally included in a kit. An ancillary reagent such as buffers, enzymes, washing solutions, hybridization solutions, detectable labels, detection reagents and the like are also optionally included.

Assay compositions are provided according to embodiments described herein which include amplified target nucleic acids containing a multinucleotide repeat region, the amplified target nucleic acids including a first label and a second label, the first label independent of the number of multinucleotide repeats and the second label proportional to the number of multinucleotide repeats, wherein the first and second labels are each independently incorporated in the amplified target nucleic acids during the amplifying or after the amplifying, and wherein the amplified target nucleic acids are bound to a capture probe specific for the amplified target nucleic acids.

Compositions and kits described herein are useful, for example, in performing methods for determining the length of a multinucleotide repeat region substantially as described herein.

Embodiments of inventive compositions and methods are illustrated in the following examples. These examples are provided for illustrative purposes and are not considered limitations on the scope of inventive compositions and methods.

Example 1

In an exemplary method, sample DNA 1 is divided into two aliquots, each of which is processed independently through the assay until fluorescent data from each path is processed to generate one or more ratios. A first process of one aliquot of the sample 1 starts with repeat-specific primer PCR amplification 3. The repeat-specific primer pair 2 includes one primer that hybridizes to the target DNA outside of the multinucleotide repeat region and a second primer that hybridizes to a plurality of regions within the repeat region. The non-repeat primer in this example is end-labeled to facilitate subsequent detection of the PCR product molecules. In this case, the end-label is biotin. The reaction product in this scenario is a heterogenous population of end-labelled nucleic acids containing variable numbers of multinucleotide repeat motifs. Later in the process, biotin will be bound to streptavidin labeled with a detectable tag. Alternative end-labels can be used, including molecules that, like biotin, become detectable upon binding to a partner as well as molecules that are inherently detectable. The PCR reagents kit 7 includes a polymerase enzyme, nucleotides and buffers.

Amplified repeat-specific product DNA 4, is then specifically captured and subjected to an encoded particle hybridization assay 5. The specific capture can be, for example, based on a complementary nucleotide sequence, or other binding-partner interactions. Hybridization reagents 8 include a hybridization buffer, a wash buffer, and a fluorescent reporter. In this specific example, the fluorescent reporter is streptavidin-phycoerythrin, the standard reporter for Luminex assays. Amplified repeat-specific DNA molecules are specifically captured onto the encoded particle set with immobilized oligonucleotide capture molecules 16. The hybridization assay 5 results in generation of amplified repeat-specific DNA fluorescent signal data 6.

The second aliquot of the sample 1 is processed in parallel using the same process but different PCR primers. Target amplification 10 is performed using a target-straddling PCR primer pair 9. Target amplification and repeat-specific amplification are shown as simultaneous processing in FIG. 1A. It is understood that in practice, the amplifications can be performed simultaneously, consecutively, in an overlapping manner, according to user preference. This produces amplified target DNA 11 that is hybridized with capture molecules. The encoded particle set 17 can be the same as that in 16, for example, when the capture region of the two amplified DNA samples is the same. The hybridization 12 produces amplified target DNA fluorescent signal data 13.

Figure 9:
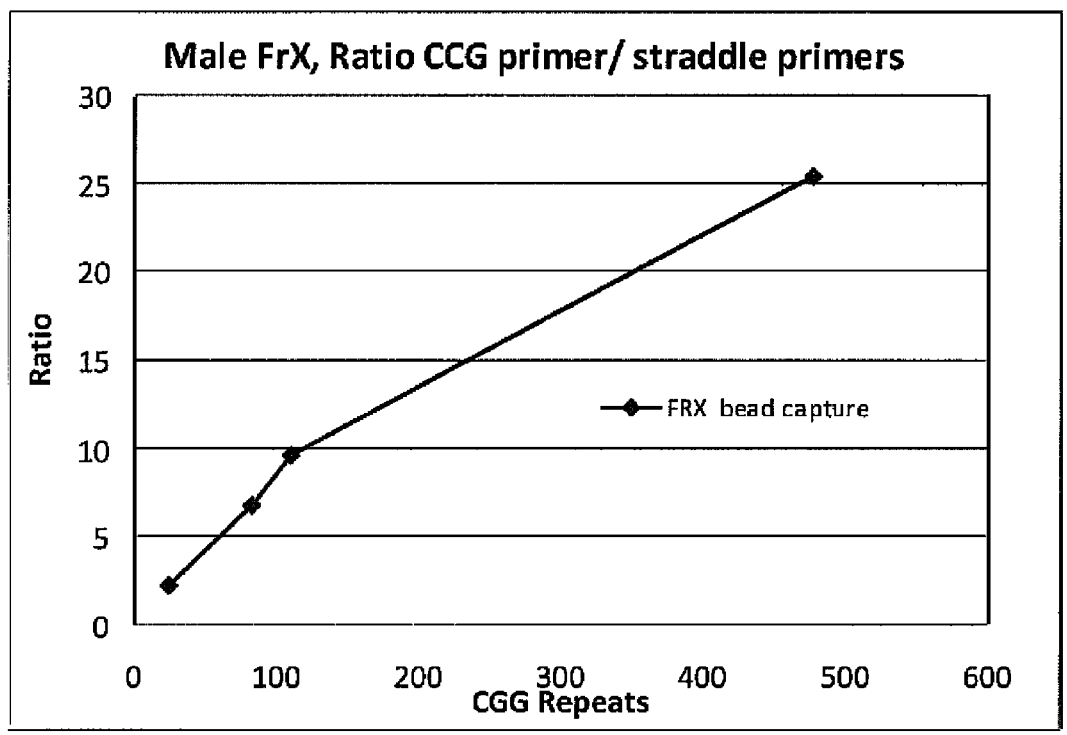
FIG. 9 is a data plot of assay results generated from Coriell Fragile X cell line reference samples with known repeat lengths using the exemplary method depicted in FIG. 1A.

The amplified repeat-specific DNA fluorescent signal data is then ratioed to the target DNA fluorescent signal data. By using a ratio of the two signals variations in the yield of the two PCR processes are compensated. FIG. 9 shows that the ratio of fluorescent signals is substantially proportional to the repeat content of male Fragile X samples from 25 to about 500 repeats.

Thus, the methods described herein can be used to determine the length of the multinucleotide repeat region that is between about 25 and about 500 repeats. For example, the length of the multinucleotide repeat region can be between about 200 and about 500 repeats, and about 300 and about 500 repeats.

Figure 2:
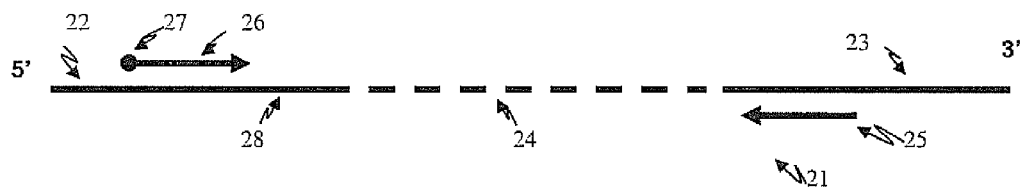
FIG. 2 is a schematic drawing depicting an exemplary configuration of a target-straddling primer pair.

FIG. 2 depicts an exemplary PCR configuration for a target-straddling primer pair and target DNA. The target sequence 21 includes a multinucleotide repeat sequence 24 that can be of variable length, depending on the genetic locus of the individual. The repeat region is flanked by non-repeat sequences 22 and 23 on the 5' and 3' ends, respectively. Target-straddling primers 25 and 26 are complementary to the non-repeat sequences that flank the repeat region. In this example the 5' primer is end-labeled with biotin 27 to facilitate subsequent detection of the PCR products (also referred to as amplified target DNA molecules) with a fluorescent streptavidin-phycoerythrin reporter. Also in this example the primer on the 5' end is located such that there is a capture 28 sequence between the end of the primer and the beginning of the repeat region. This sequence is used for the subsequent hybridization capture of PCR products.

Figure 3:
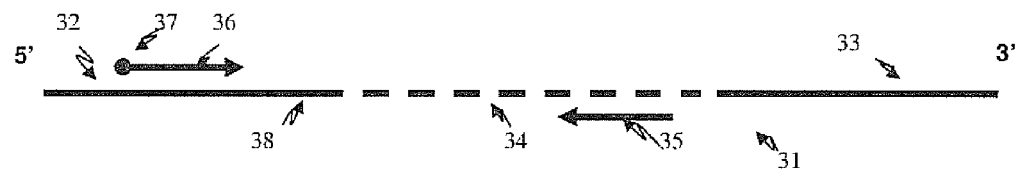
FIG. 3 is a schematic drawing depicting an exemplary configuration of a repeat-specific primer pair, in which the non-repeat primer is upstream from the repeat-specific primer.

FIG. 3 depicts an exemplary PCR configuration for a repeat-specific primer pair and repeat-specific DNA. The target sequence 31 includes a multinucleotide repeat sequence 34 can be of variable length, depending on the genetic locus of the individual. The repeat region is flanked by non-repeat sequences 32 and 33 on the 5' and 3' ends, respectively. The 5' non-repeat primer 36 is located 5' of the repeat region 34, and in this example the primer is end-labeled with biotin 37 to facilitate detection of the resulting PCR product DNA (also referred to as amplified repeat-specific DNA molecules). The non-repeat primer is defined so that there is a region of non-repeat DNA 38 between the non-repeat primer and the repeat region, where this non-repeat region can be used for subsequent capture or detection of the resulting PCR products. This non-repeat primer can be the same as a 5' target-straddling primer described above. The second primer 35 is repeat-specific primer, meaning that it hybridizes to the repeat region. Such a repeat primer can hybridize at any of a large number of locations along the repeat region.

Figure 4:
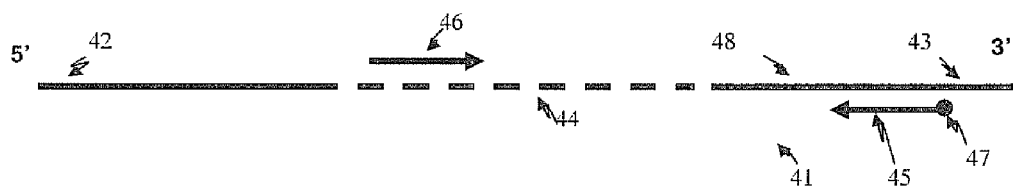
FIG. 4 is a schematic drawing depicting an exemplary configuration of a repeat-specific primer pair, in which the non-repeat primer is downstream from the repeat-specific primer.

FIG. 4 depicts an exemplary alternate PCR configuration similar to that of FIG. 3 except that the relative locations of the non-repeat and repeat primers are reversed. The target sequence 41 includes a repeat sequence 44 that can have variable length. The repeat region is flanked by non-repeat sequences 42 and 43 on the 5' and 3' ends, respectively. The 3' non-repeat primer 46 is located 3' of the repeat region 44, and in this example the primer is end-labeled with biotin 47 to facilitate detection of the resulting PCR product DNA (also referred to as amplified repeat-specific DNA molecules). The non-repeat primer is defined so that there is a region of non-repeat DNA 48 between the non-repeat primer and the repeat region, where this non-repeat region can be used for subsequent capture or detection of the resulting PCR products. This non-repeat primer can be the same as the 5' target straddling primer described above. The second primer 46 is repeat-specific primer, meaning that it hybridizes to the repeat region. Such a repeat-specific primer can hybridize at any of a large number of locations along the repeat region.

Figure 5A:
FIG. 5A is a schematic drawing depicting an amplified target DNA molecule prepared using a target-straddling primer pair as depicted in FIG. 2.
Figure 5B:
FIG. 5B is a schematic drawing depicting an amplified repeat-specific DNA molecule prepared using a primer pair as depicted in FIG. 3.
Figure 5C:
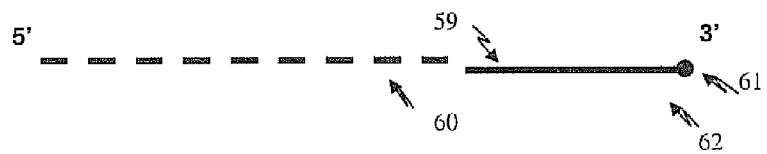
FIG. 5C is a schematic drawing depicting an amplified repeat-specific DNA molecule prepared using a primer pair as depicted in FIG. 4.

FIG. 5A depicts an amplified DNA molecule 52 produced by the PCR configuration of FIG. 2. This amplified target DNA molecule contains a biotin label 50 on the 5' end, a 5' non repeat sequence 53, a repeat region of variable length 51, and a 3' non-repeat region 54. FIG. 5 B depicts an amplified DNA molecule 58 produced by the PCR configuration of FIG. 3. This amplified repeat-specific DNA molecule contains a biotin label 55 on the 5' end, a 5' non-repeat sequence 56, and a repeat sequence 57 of variable length. FIG. 5C depicts an amplified DNA molecule produced by the PCR configuration of FIG. 4. This amplified repeat-specific DNA molecule contains a biotin label 61 on the 3' end, a 3' non-repeat sequence 59, and a repeat sequence 60 of variable.

Figure 6:
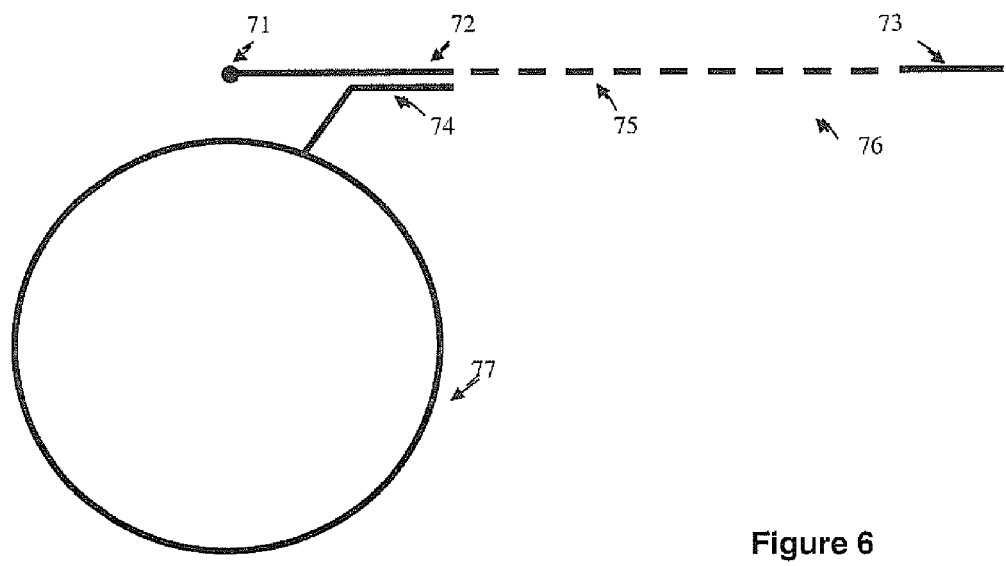
FIG. 6 is a schematic drawing of an amplified target DNA molecule specifically bound to an oligonucleotide capture molecule immobilized on an encoded particle.

FIG. 6 depicts, schematically, a single oligonucleotide capture molecule immobilized on an encoded particle, with a bound amplified target DNA molecule from PCR configurations such as that shown in FIG. 5A. An encoded particle 77, such as Luminex xMAP bead, in this example, has a large number of oligonucleotide capture molecules 74 coupled to its surface (only one molecule is shown in this figure). The capture oligonucleotide 74 is designed to be complementary to a non-repeat region 72 of a target DNA molecule 76 produced by the approach described above. The captured amplified target DNA molecule contains a detectable label 71, biotin in this example, on one end and contains a repeat region 75 and a non-repeat region 73.

Figure 7:
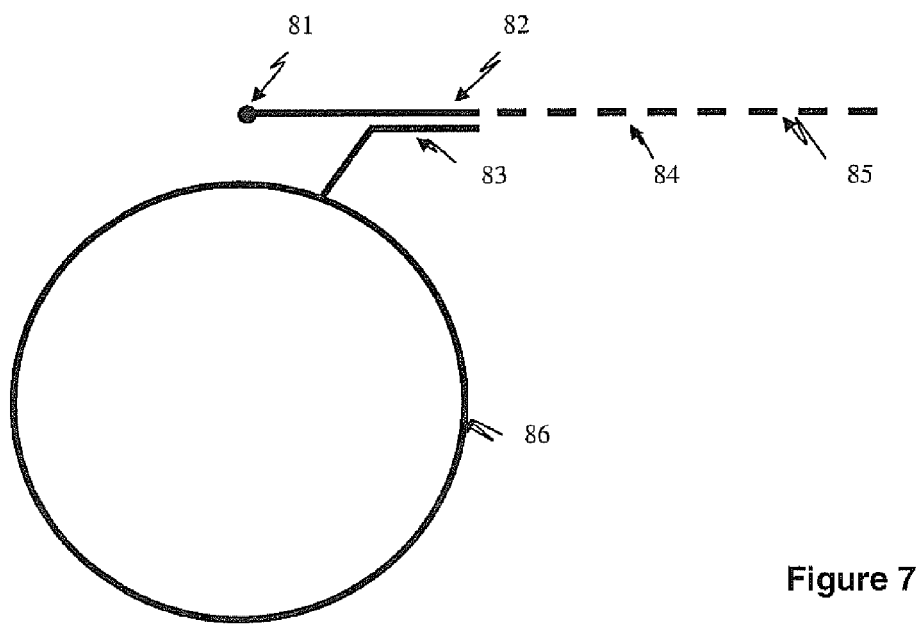
FIG. 7 is a schematic drawing of an amplified repeat-specific DNA molecule specifically bound to an oligonucleotide capture molecule immobilized on an encoded particle.

FIG. 7 depicts, schematically, a single oligonucleotide capture molecule immobilized on an encoded particle with a bound amplified repeat-specific DNA molecule. An encoded particle 86, such as a Luminex xMAP bead in this example, has a large number of oligonucleotide capture molecules 83 coupled to its surface (only one molecule is shown in this figure). The capture oligonucleotide 83 is designed to be complementary to a non-repeat region 82 of the repeat-specific DNA molecules produced by a repeat-specific primers such as those described by FIG. 5B or 5C. The captured repeat-specific DNA molecule has a detectable label 81, biotin in this example, on one end, and a repeat region 84.

Figure 8:
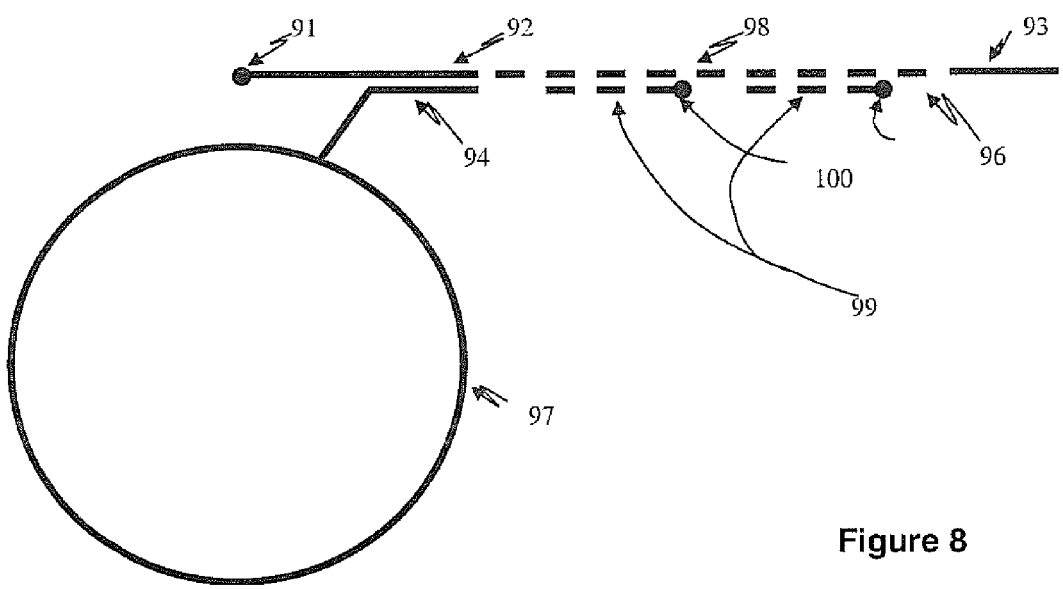
FIG. 8 is a schematic drawing of an amplified target DNA molecule hybridized with two repeat-detector probes and specifically bound to an oligonucleotide capture molecule immobilized on an encoded particle.

FIG. 8 depicts, schematically, a single oligonucleotide capture molecule immobilized on an encoded particle, and a single amplified target DNA molecule from one of the PCR configurations such as those shown in FIG. 5. An encoded particle 97, such as a Luminex xMAP bead in this example, has a large number of oligonucleotide capture molecules 94 coupled to its surface (only one molecule is shown in this figure). The capture oligonucleotide 94 is designed to be complementary to a non-repeat region 92 of an amplified target DNA molecule produced by target straddling primer pair as described in FIG. 5A. The captured amplified target DNA molecule has a detectable label 91, biotin in this example, on one end, and has a repeat region 98.

Also hybridized to the amplified target DNA molecule 96 are one or more repeat-detector probes 99. One or more detectable labels 100, biotin in this example, are incorporated into each repeat-detector probe. The repeat-detector probe molecules are complementary to the repeat region 98 and a plurality of repeat-detector probes can hybridize to the repeat region. The repeat-detector probes can be hybridized with the amplified target DNA molecules together with or after the amplified target DNA molecules have been captured by the beads.

Notably, the longer the repeat region in the captured amplified target DNA molecule, the more labeled repeat-detector probes will hybridize to it and the larger the signal that will be generated and detected. Accordingly, the present method produces fluorescent signals in proportion to the length of the multinucleotide repeat region contained in the amplified target DNA molecule.

FIG. 9 is example data from a first example assay according to the process outlined in FIG. 1. The values along the horizontal axis are the number of CGG repeats according to the supplier of cell line DNA samples (Coriell Institute for Medical Research, Trenton N.J.). The samples represent males with Fragile X repeat lengths of 25, 83, 110 and 477. The values along the vertical axis of the plot are the ratio as calculated according to the first example, the ratio of the fluorescent signal generated by repeat-specific DNA divided by the fluorescent signal of amplified target DNA of the same sample. The ratio data increases monotonically and approximately linearly with repeat region length through this range.

Example 2

FIG. 1B is a schematic process flow chart showing another exemplary method for determining the length of a multinucleotide repeat region in a target DNA molecule.

Referring to FIG. 1B in detail, sample DNA 114 is PCR amplified 102 using target-straddling primers 111 and a PCR reagents kit 101. Amplified target DNA molecule 103 is produced, and two aliquots of this product are then directed through two assay paths. A first aliquot is subjected to a repeat-detection probe assay 106 as is shown in FIG. 8. Repeat-detection probes 105, an encoded particle set with immobilized capture oligonucleotides 115 and hybridization reagents 106 are combined and hybridized. The hybridization reagents include hybridization buffers, wash buffers, and a streptavidin-phycoerythrin fluorescent reporter that specifically binds to the biotin labels previously incorporated. Alternatively, the encoded particle set with immobilized probes and the repeat-detector probes can be hybridized sequentially in either order. The repeat-detection probes hybridize to the amplified target DNA molecule in approximate proportion to the repeat region length, plus one extra label from the end label on the amplified target DNA molecule. When the product of this assay is read in the appropriate detection instrument, a Luminex 200 in this example, repeat-detection probe fluorescent signal data 107 is produced.

The second aliquot of target DNA is processed with a similar assay that omits the repeat-detection probe. The encoded particle straddling primer assay 112 has inputs of the amplified target DNA molecule 103, the same encoded particle set with immobilized probes 115, and the hybridization reagents 110. Using the same assay protocol, this version produces amplified target DNA molecule fluorescent signal data 113 from one biotin label on each PCR product molecule regardless of the repeat region length.

For each sample, a ratio of the amplified repeat-specific DNA molecule fluorescent signal data 107 to the amplified target DNA molecule fluorescent signal data 113 is calculated. By calculating the ratio with the amplified target DNA molecule fluorescent signal data in the denominator, sample repeat data is generated, a close representation of the length of the multinucleotide repeat region as is shown in the example data below.

Figure 10:
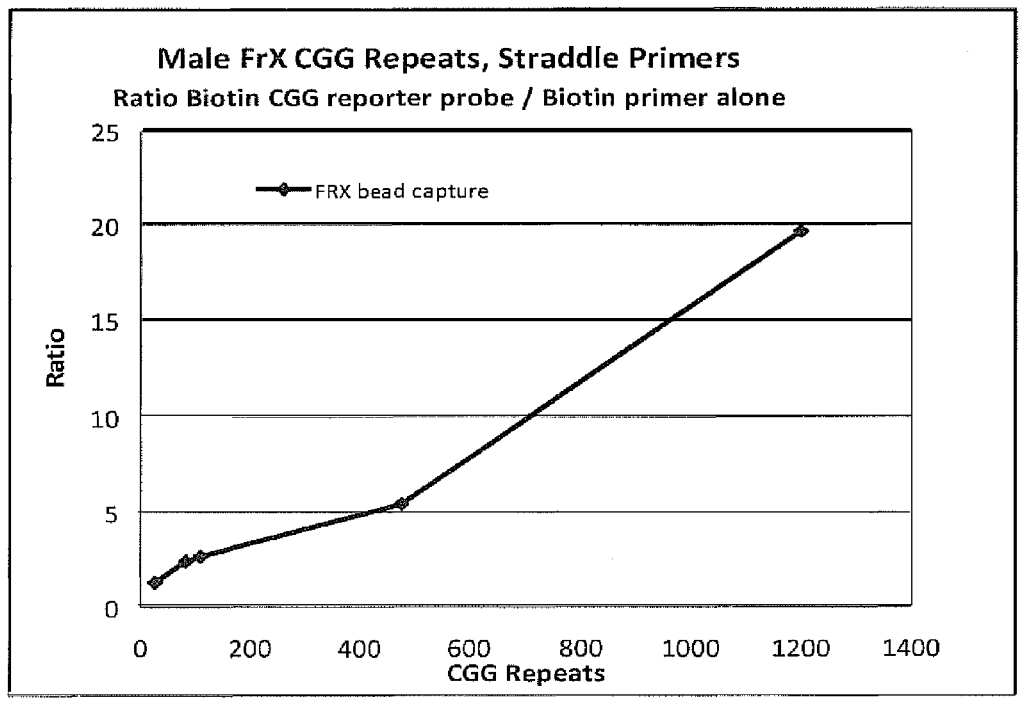
FIG. 10 is a plot of assay results generated from Coriell Fragile X cell line reference samples with known repeat lengths using the exemplary method depicted in FIG. 1B.

FIG. 10 is example data from a second example assay according to the process outlined in FIG. 1B. The values along the horizontal axis are the number of CGG repeats according to the supplier of cell line DNA samples (Coriell Institute for Medical Research, Trenton N.J.). The samples represent males with Fragile X repeat lengths of 25, 83, 110, 477 and 1,200. The values along the vertical axis of the plot are the ratio as calculated according to the second example, the ratio of the fluorescent signal generated by hybridized repeat-detector probes divided by the fluorescent signal of amplified target DNA of the same sample. The ratio data increases monotonically and approximately linearly with repeat length throughout this range.

Example 3

The example shows a protocol for determining the length of a multinucleotide repeat region of a Fragile X gene target DNA molecule.

PCR Materials
PCR reagent kit: Fast Start TAQ Polymerase (Cat #12 032 902 001 or 12032937001, Roche Molecular, Indianapolis, Ind.)
5 M betaine (Sigma-Aldrich, St Louis, Mo.)
Normal Male DNA (Promega, Madison, Wis.) Normal Female DNA (Promega)
Straddle Primers (Eurofins MWG Operon, Huntsville, Ala.) (the source for all oligo nucleotides in this disclosure)

5' Primer:
(SEQ ID No. 9)
[Biotin-5]GCTCAGCTCCGTTTCGGTTTCACTTCCGGT

3' Primer:
(SEQ ID No. 10)
AGCCCCGCACTTCCACCACCAGCTCCTCCA

CCG Repeat Primers
5' Primer: [Biotin-5]GCTCAGCTCCGTTTCG-GTTTCACTTCCGGT (SEQ ID No. 9) (same as 5' straddle primer above)

3'CCGPRIMER-
CTCGAGGCCCAGCCGCCGCCGCCG    (SEQ ID No. 15)

PCR of Sample DNA
Make up PCR mix using Roche Fast Start
On ice make up PCR premix as follows
Premix for 1 reaction, volume 25 µL:
9 µL dH$_2$O
10 µL 5M Betaine
2.5 µL 10×PCR reaction buffer (with 20 mM MgCl$_2$)
1.25 µL 10 mM dNTP mix
0.75 µL 10 µM Primer 1
0.75 µL 10 µM Primer 2
0.25 µL 5 µL Taq DNA Polymerase
0.5 µL Template (sample DNA) at 100-300 ng/µL
Or, premix for 10 reactions, volume 50 µL:
180 µL dH$_2$O
200 µL 5M Betaine
5 µL 10×PCR reaction buffer (with 20 mM MgCl$_2$)
2.5 µL 10 mM dNTP mix
15 µL 10 µM Primer 1
15 µL 10 µM Primer 2
5 µL 5 U/µL Taq DNA Polymerase
Dispense 49 µL of premix+sample DNA into thin wall PCR tubes or plate on ice
Add 1 µl of Male and Female reference at 100-300 ngs/µL to each well with straddle primers and CGG Repeat Primers.
Cap tubes or plate appropriately.
Place tubes on Cycler and run FMR1 PCR profile (estimated time 6 hours).
Remove tubes from cycler. Store at −20° C. or continue to Gel Analysis
PCR cycling (PTC100, MJ Research, Watertown, Mass.):
98° C. for 10 min
10 cycles at:
97° C. for 35 sec,
64° C. for 35 sec,
68° C. for 4 min.
25 cycles at:
97° C. for 35 sec,
64° C. for 35 sec,
68° C. for 4 min, plus 20 sec incremental extension for each cycle.
68° C. for 10 min
4° C. hold
Luminex Bead Hybridization
Immobilized capture molecule 5' CTGGCAGCGGCGC-CTCCGTCAC (SEQ ID No. 16) Bead Code 27 and/or 28
Oligo to bead coupling per standard Luminex EDC protocol
Hybridization Reagents

| 1.5 X TMAC Hybridization Buffer 250 mL Reagent | Catalog Number | Final Concentration | Amount/ 250 mL |
|---|---|---|---|
| 5 M TMAC | Sigma T3411 | 4.5 M | 225 mL |
| 20% Sarkosyl solution | Sigma L7414 | 0.15% | 1.88 mL |
| 1 M Tris-HCl, pH 8.0 | Sigma T3038 | 75 mM | 18.75 mL |
| 0.5 M EDTA, pH 8.0 | Invitrogen 15575-020 | 6 mM | 3.0 mL |
| H$_2$O | — | — | 1.37 mL |

Streptavidin-phycoerythrin reporter PJRS34 DH23 012 2.02 mgs/mL (Prozyme, San Leandro, Calif.)
Wash Buffer 1×PBS, 0.01% Tween-20
Make up Hybridization Premix
Premix for 1 sample, 33 µL/PCR-product sample:
32 µL 1.5M TMAC hybridization buffer
1 µL 5' Capture CTGGCAGCGGCGCCTCCGTCAC (SEQ ID No. 16) Bead at 1000 beads/µL
Premix for 10 samples:
320 µL 1.5×TMAC
10 µL capture molecule_CTGGCAGCGGCGCCTCCGT-CAC (SEQ ID No. 16) beads at 1000 beads/µL
330 µL Total
Vortex premix vigorously immediately before dispensing.
Hybridization and Analysis
Dispense 34 µl hybridization premix/well to be hybridized into PCR tubes or plate. Add 2 µL of each PCR product (straddle primer or repeat primer PCR product). Add 15 µL dH$_2$O Final volume 50 µL. Seal tubes with caps or plate with foil sealer. Place on thermal cycler and denature at 95° C. for five minutes. Cool to 50° C., hold for 15 minutes.
Remove hybridization reactions from cycler and add 100 µL wash buffer. Transfer buffer and hybridization solution to 0.45 umicron Multiscreen filter plate MSHVN4510 (Millipore, Bedford Mass.). Apply vacuum to filter plate bottom to aspirate liquid. Add 100 µL wash buffer. Apply vacuum. Repeat step 7 one time.
Add 100 µL streptavidin-phycoerythrin reporter at 4 ug/ml in BSA diluent to each well. Wash wells with 100 µL buffer. Apply vacuum to remove liquid.
Dry Filter plate bottom with absorbent pad.
Add 100 µL wash buffer to resuspend beads and read on Luminex 200 instrument with appropriate template.
Calculate ratio of repeat primer PCR product to straddle PCR product fluorescence signals for each sample. Compare sample ratios to those produced by standards in the run.

Example 4

This example shows a protocol for determining the length of a multinucleotide repeat region of a Fragile X gene target DNA molecule.

PCR Materials
PCR reagent kit: Fast Start TAQ Polymerase (Cat #12 032 902 001 or 12032937001, Roche Molecular, Indianapolis, Ind.)
5 M betaine (Sigma-Aldrich, St Louis, Mo.)
Normal Male DNA (Promega, Madison, Wis.)
Normal Female DNA (Promega)
Straddle Primers (Eurofins MWG Operon, Huntsville Ala.) (the source for all oligo nucleotides in this disclosure):

```
5' Primer:
                                       (SEQ ID No. 9)
[Biotin-5]GCTCAGCTCCGTTTCGGTTTCACTTCCGGT 3' Primer:
                                      (SEQ ID No. 10)
AGCCCCGCACTTCCACCACCAGCTCCTCCA
```

PCR of Sample DNA
Make up PCR mix using Roche Fast Start
On ice make up PCR premix as follows:
Premix for 1 reaction, volume 25 µL:
   9 µL dH$_2$O
   10 µL 5M Betaine
   2.5 µL 10×PCR reaction buffer (with 20 mM MgCl$_2$)
   1.25 µL 10 mM dNTP mix
   0.75 µL 10 µM Primer 1
   0.75 µL 10 µM Primer 2
   0.25 µL 5 U/µL Taq DNA Polymerase
   0.5 µL Template (sample DNA) @ 100-300 ng/µL
Or, premix for 10 reactions, volume 50 µL:
   180 µL dH$_2$O
   200 µL 5M Betaine
   5 µL 10×PCR reaction buffer (with 20 mM MgCl$_2$)
   2.5 µL 10 mM dNTP mix
   15 µL 10 µM Primer 1
   15 µL 10 µM Primer 2
   5 µL 5 U/µL Taq DNA Polymerase Dispense 49 µL of premix+sample DNA into thin wall PCR tubes or plate on ice. Add 1 µl of Male and Female reference at 100-300 ngs/µL to each well with straddle primers and CGG Repeat Primers. Cap tubes or plate appropriately. Place tubes on Cycler and run FMR1 PCR profile (estimated time 6 hours). Remove tubes from cycler. Store at 20° C. or continue to Gel Analysis PCR cycling (PTC100, MJ Research, Watertown, Mass.):
   98° C. for 10 min
   10 cycles at:
   97° C. for 35 sec,
   64° C. for 35 sec,
   68° C. for 4 min.
   25 cycles at:
   97° C. for 35 sec.
   64° C. for 35 sec.
   68° C. for 4 min, plus 20 sec incremental extension for each cycle.
   68° C. for 10 min
   4° C. hold
Luminex Bead Hybridization
Immobilized capture molecule 5' CTGGCAGCGGCGCCTCCGTCAC (SEQ ID No. 16) Bead Code 27 and/or 28
Oligo to bead coupling per standard Luminex EDC protocol
Biotin repeat motif reporter probe Biotin-CCGCCGCCGCCG (SEQ ID No. 17)

Hybridization Reagents

| 1.5 X TMAC Hybridization Buffer 250 mL Reagent | Catalog Number | Final Concentration | Amount/ 250 mL |
|---|---|---|---|
| 5 M TMAC | Sigma T3411 | 4.5 M | 225 mL |
| 20% Sarkosyl solution | Sigma L7414 | 0.15% | 1.88 mL |
| 1 M Tris-HCl, pH 8.0 | Sigma T3038 | 75 mM | 18.75 mL |
| 0.5 M EDTA, pH 8.0 | Invitrogen 15575-020 | 6 mM | 3.0 mL |
| H$_2$O | — | — | 1.37 mL |

Streptavidin-phycoerythrin reporter PJRS34 DH23 012 2.02 mgs/mL (Prozyme, San Leandro, Calif.)
Wash Buffer 1×PBS, 0.01% Tween-20
Make up Hybridization Premixes 1 & 2
10× Hybridization premix 1 (for measuring straddle primer product)
320 µL 1.5×TMAC
10 µL Capture_CTGGCAGCGGCGCCTCCGTCAC (SEQ ID No. 16) Bead at 1000 beads/µL
330 µL Total
Vortex vigorously immediately before dispensing.
10× Hybridization premix 2 (for measuring repeat length with repeat motif reporter probe)
319 µL 1.5×TMAC
10 µL Capture_CTGGCAGCGGCGCCTCCGTCAC (SEQ ID No. 16) Bead at 1000 beads/µL
1 µL Biotin reporter CCGCCGCCGCCG (SEQ ID No. 17) 100 µM
330 µL Total
Vortex vigorously immediately before dispensing.
Hybridization Procedure
Dispense 33 µl/well Hybridization Premix 1 and Premix 2 for each PCR product into separate PCR tubes or plate wells. Add 2 µL of each straddle primer PCR product to one well with Hyb Premix 1 and one well with Hyb Premix 2. Add 15 µL dH$_2$O to all hybridization wells. Mix by pipetting up and down. Seal tubes with caps or plate with foil plate sealer. Place on thermal cycler and denature @ 95° C. for five minutes. Cool to 50° C. and hold for 15 minutes. Remove hybridization reactions from cycler and add 100 µL wash buffer. Transfer wash buffer plus hybridization mixture to 0.45 umicron Multiscreen filter plate MSHVN4510 (Millipore. Bedford Mass.). Apply vacuum to filter plate bottom to aspirate liquid. Add 100 µL wash buffer. Apply vacuum. Repeat step 7 one time. Add 100 µL streptavidin-phycoerythrin reporter at 4 µg/ml in BSA diluent to each well. Wash wells with 100 µL buffer. Apply vacuum to remove liquid. Dry Filter plate bottom with absorbent pad. Add 100 µL wash buffer to resuspend beads and read on Luminex 200 instrument with appropriate template. Calculate ratio of repeat motif reporter probe to straddle PCR product fluorescence signals for each sample. Compare sample ratios to those produced by standards in the run.

Example 5

Figure 1C:
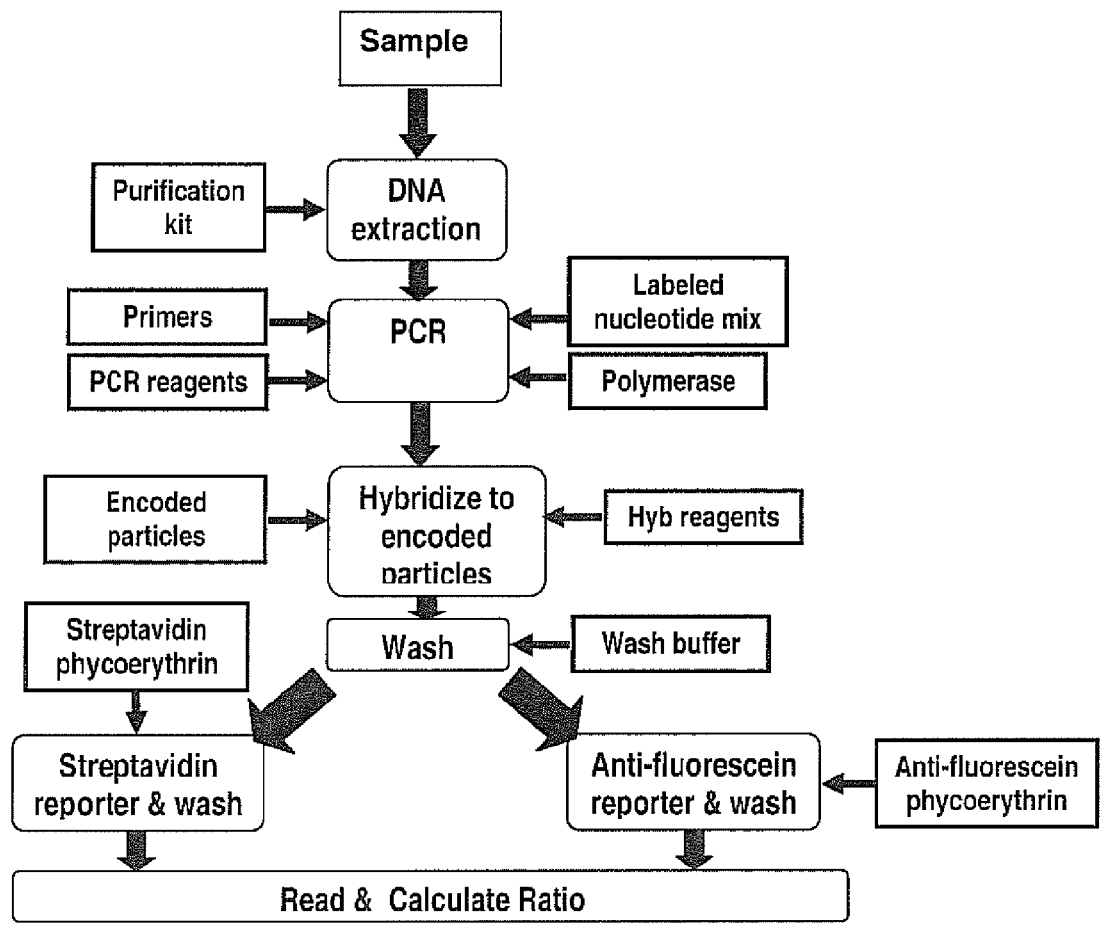

FIG. 1C is a schematic process flow chart showing another exemplary method for determining the length of a multinucleotide repeat region in a target DNA molecule.

Referring to FIG. 1C, sample DNA is PCR amplified using target-straddling primers and a labeled nucleotide mix. The labeled nucleotide mix can contain any deoxynucleotide contained in the multinucleotide repeat sequence, and can have any direct or indirect label so long as the label can be attached to a deoxynucleotide without affecting the function of the deoxynucleotide, the ability for the deoxynucleotide to be incorporated into a nucleic acid by a DNA polymerase, or the function of the label. In an exemplary case, the labeled nucleotide mix contains biotinylated dCTP. The target-straddling primer paid contains a primer containing a target-detection label. The target-detection label and the repeat-detection label can be any label that is detectable or can be rendered detectable by a treatment or by binding to a reporter. In an exemplary case, the target-detection label is fluorescein. A reporter useful for rendering fluorescein detectable is anti-fluorescein antibody conjugated with phycoerythrin. Amplified target DNA molecule is produced, and hybridized to encoded particles. Hybridization can be between a multinucleotide repeat sequence in the amplified target nucleic acid molecule, and a complementary sequence attached to the encoded particles. The hybridized encoded particles are aliquoted. One aliquot is incubated with a reporter probe that binds to the biotin moieties of the amplified target nucleic acid (for example, streptavidin conjugated to a detectable moiety, such as streptavidin conjugated to phycoerythrin), and another aliquot is incubated with a reporter probe that binds to a label imparted by one of the target-straddling primers.

Thus, as is exemplified in FIG. 11, detectable labels incorporated or bound at regular intervals along the length of the repeat region will indicate the length via the aggregate signal strength. To summarize in brief, a PCR amplification of the repeat region of the target DNA is performed. During this process, a detectable label (biotin) is incorporated into PCR products. The signal ultimately produced by the detectable label is proportional to the length of the repeat region amplified. There is also a detectable label (fluorescein as a hapten) on one primer used to amplify the PCR product. The signal ultimately produced by this detectable label is essentially 1 signal per PCR product. The PCR products are captured onto encoded particles such as Luminex beads and the two labels are separately detected. The incorporated label corresponding to the repeat-detection label corresponds to an average number of CGG repeats. The incorporated label corresponding to the target-detection label (i.e. Primer label) corresponds to the number of PCR product molecules. It is possible to then calculate the ratio of the two detectable labels. The ratio approach allows for normalizing for the decrease in PCR yields as repeat lengths increase.

An additional feature of the above described embodiment is that the fluorescein label on one primer, while used as a hapten in the present hybridization assay, can also be used as a directly detected label in capillary electrophoresis. This allows the alternative of using a first portion the PCR products made according to this example to be used in the hybridization assay, for example in a screening assay setting, while utilizing a second portion to be evaluated by capillary electrophoresis as a second test for samples that tested positive in a hybridization assay as is described herein.

Figure 12A:
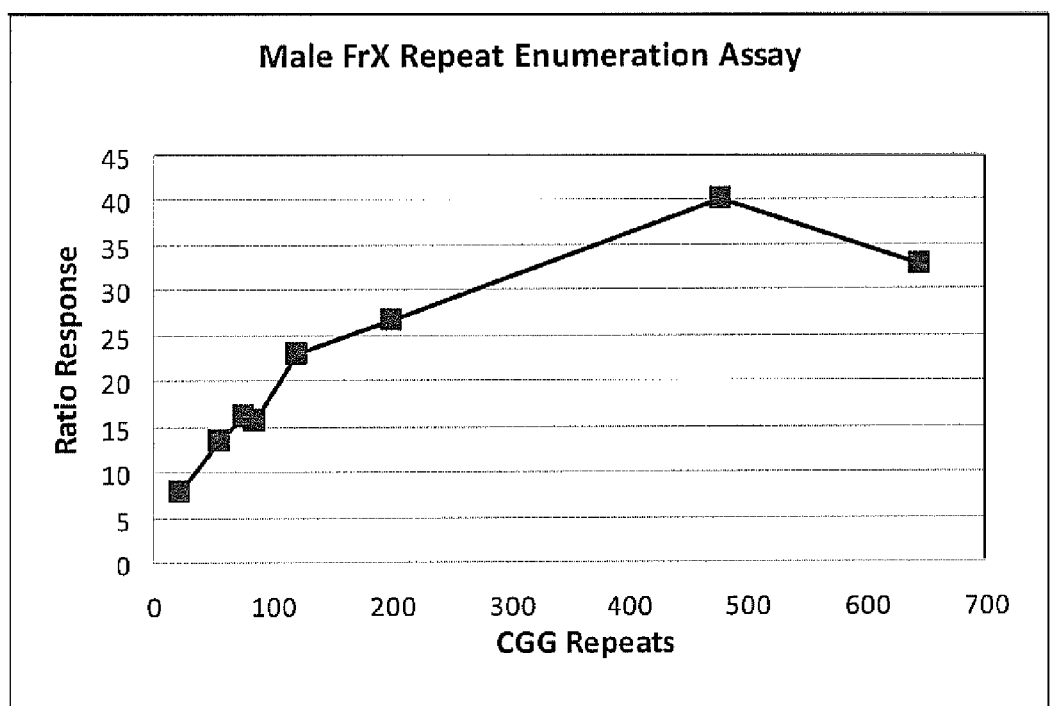
FIG. 12 is a data plot of assay results using the exemplary method depicted in FIG. 11 for male reference samples (FIG. 12A) and female reference samples performed under a first set of hybridization conditions (FIG. 12B) and a second set of set of hybridization conditions (FIG. 12C)
Figure 12B:
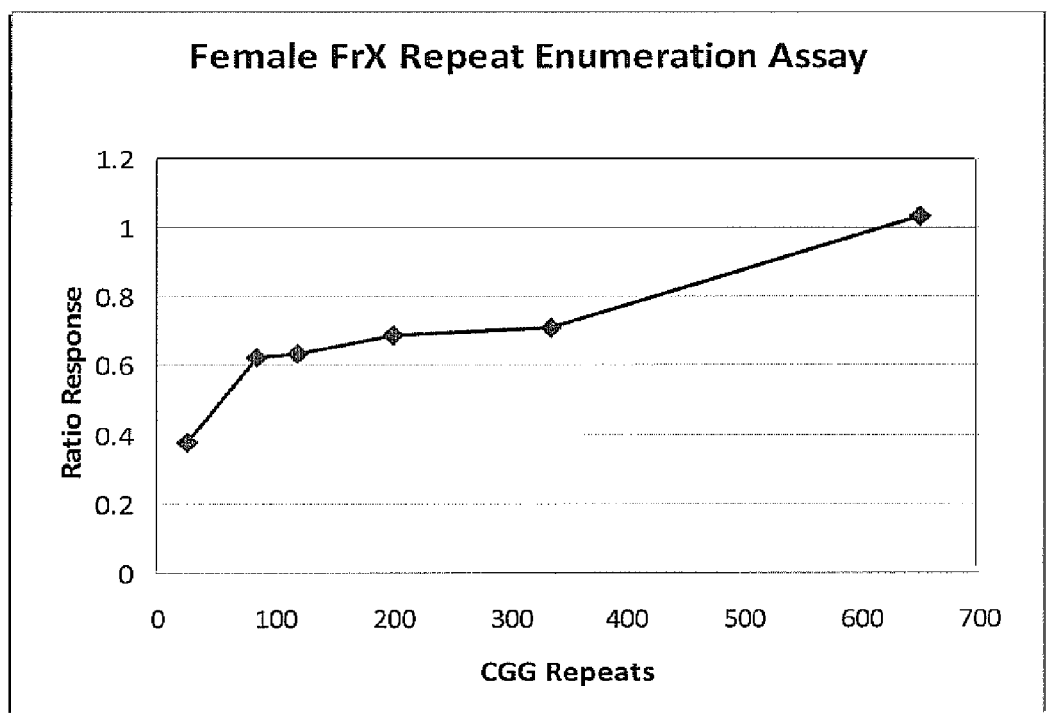

FIGS. 12A and 12B are data from a first example assay according to the process outlined in FIGS. 1C and 11. The values along the horizontal axis are the number of CGG repeats according to the supplier of cell line DNA samples (Coriell Institute for Medical Research, Trenton, N.J.). The samples represent males with Fragile X repeat lengths of between about 20 to about 650. The values along the vertical axis of the plot are the ratio of the fluorescent signal generated by the repeat-detection label divided by the fluorescent signal of amplified target DNA (derived from target-detection label) of the same sample. The ratio data increases monotonically and approximately linearly with repeat length throughout all or most of this range.

Below are exemplary protocols for experimental steps useful when determining the length of a multinucleotide repeat region of a Fragile X gene target DNA molecule, using labeled deoxynucleotides during amplification of the target DNA.

CGG Repeat Straddle Primers:

```
5' Primer 1:
                                        (SEQ ID No. 9)
GCTCAGCTCCGTTTCGGTTTCACTTCCGGT 3' Primer 2:
                                        (SEQ ID No. 10)
Fluor 5' AGCCCCGCACTTCCACCACCAGCTCCTCCA
```

100 µM Biotin dCTP
Genomic DNA 20-30 ngs/µL
PCR of Genomic DNA
Make Up PCR Mix Abbott GPR reagents & Protocol
On ice make up PCR premix as follows:
    Abbott TR Enzyme & High GC Buffer PCR
    1× Reaction Volume 25 µL
    8.15 µL dH$_2$O
    13 µL High GC PCR Buffer
    0.8 µL 10 uM Primer 1
    0.8 µL 10 uM Primer 2
    1.25 µL TR Enzyme Mix
    1 µL Biotin dCTP 100 uM
    1 µL Template at 10-30 ng/µL
    Dispense 22 µL into thin wall PCR tubes or plate on ice. Add 1 µl of at 10-30 ngs/µL to each well with straddle primers. Cap tubes or plate appropriately. Start Abbott FRX PCR profile (estimated time 6 hours). Place tubes on Cycler and place tubes in cycler as temp reaches 98.5° C. Remove tubes from cycler. Store at −20° C. or continue to Gel Analysis
PCR cycling (ABBO FRX Progr): Amplification Conditions

| Temperature | Time (min:sec) | Cycles |
|---|---|---|
| 98.5° C. | 0:10 | 15 |
| 58.0° C. | 1:00 | |
| 75.0° C. | 6:00 | |
| 98.5° C. | Auto extend | |
| 0.1° C./cycle* | 0:10 | 15 |
| 56.0° C. | 1:00 | |
| 75.0° C. | 6:00 | |
| 4.0° C. | Hold | |

*0.1 each cycle.

Gel Analysis of PCR Products:
10× Blue Juice Loading Buffer Invitrogen
2 Log DNA Ladder NEB
2.0% Agarose eGel. Invitrogen Cat G5618-02
1) Pre-run 2.0% agarose eGel as manufacturer recommends.
2) Make up 0.5× blue juice sufficient for the number of sample to be run or use current stock.
3) Make up DNA markers using 2 log DNA ladder from NEB at 300 ngs/10 µl in 0.5× Blue or use current dilution.
4) Add 5 µl of each PCR sample reaction Straddle and CGG repeat primer product to a separate tubes.
5) Add 15 µl of 0.5× Blue juice to each tube for gel analysis. Mix samples by vortexing
6) Add 10 µl of 2 Log ladder to a well of 2.0% agarose eGel.
7) Add 20 µl of each PCR in loading buffer.
8) Run gel for 30 minutes using preset command on eGel apparatus.
Capture Gel image on Kodak Image Station
Filter setting 4 F stop 1.2, Zoom 25, Focus 5 (1.5)
Exposure; 20 sec 8 times
Save image for documentation.

Hybridization

1) Dispense 23 µl/well of Hyb premix into PCR tubes or plate.
2) Add 2 µL (1:3 Dilution) of each PCR product into individual wells.
3) Seal tubes with caps or plate with plate foil.
4) Place on thermal cycler and denature at 100° C. for five minutes
5) Cycle to 50° C. for 30 minutes.
6) Remove hybridization reactions from cycler and add 100 µL Wash
7) Split the hybridized PCR by transferring 50 µl Wash Hyb Mix into 2 wells of 0.4 umicro Millipore filter plate. Apply vacuum to remove liquid.
8) Add 100 µL Wash 2. Apply vacuum.
9) Repeat step 7 one time.
10) Add 100 µL SA PE @ 2 ug/ml in Diluent to one well of each Hybridized PCR.
11) Add 100 µL of Antifluorescien PE at 2 µg/µL in Diluent into the other well of Hybridized PCR.
12) Incubate 30 minutes with shaking.
13) Apply vacuum to remove liquid.
14) Wash wells with 100 µL Wash. Apply vacuum to remove liquid.
15) Dry Filter plate bottom with absorb pad.
16) Add 100 µL Wash and read on Luminex with appropriate template.

FRX Bead 83 & 91 CGGCGGCGGCGGCGG (SEQ ID No. 18) Capture Bead at 2000 beads/µL

| 1.5 X TMAC Hybridization Solution (MICROSPHERE DILUENT) 250 mL Reagent | Catalog Number | Final Concentration | Amount/ 250 mL |
|---|---|---|---|
| 5 M TMAC | Sigma T3411 | 4.5 M | 225 mL |
| 20% Sarkosyl solution | Sigma L7414 | 0.15% | 1.88 mL |
| 1 M Tris-HCl, pH 8.0 | Sigma T3038 | 75 mM | 18.75 mL |
| 0.5 M EDTA, pH 8.0 | Invitrogen 15575-020 | 6 mM | 3.0 mL |
| H₂O | — | — | 1.37 mL |

Prozyme SA PE PJRS34 DH-23 012 2.02 mgs/mL
Invitrogen Antifluorescien PE: Cat A21250, Lot 41973A 2 mgs/mL
Anti Fluorescein & SA PE Diluent 1×PBS 0.01% Tween 0.1% BSA
Wash 1×PBS 0.01% Tween
0.4 umicro Millipore filter plate
PCR reaction Biotin Fluorescein Method 2
Hybridization:
25 µL/Sample
10× Premix
160 µL 1.5×TMAC
80 µL dH20
2.5 µL Capture 83&91 Bead at 2000 beads/µL
250 µL Total
Vortex vigorously immediately before dispensing.

Example 6

Figure 12C:
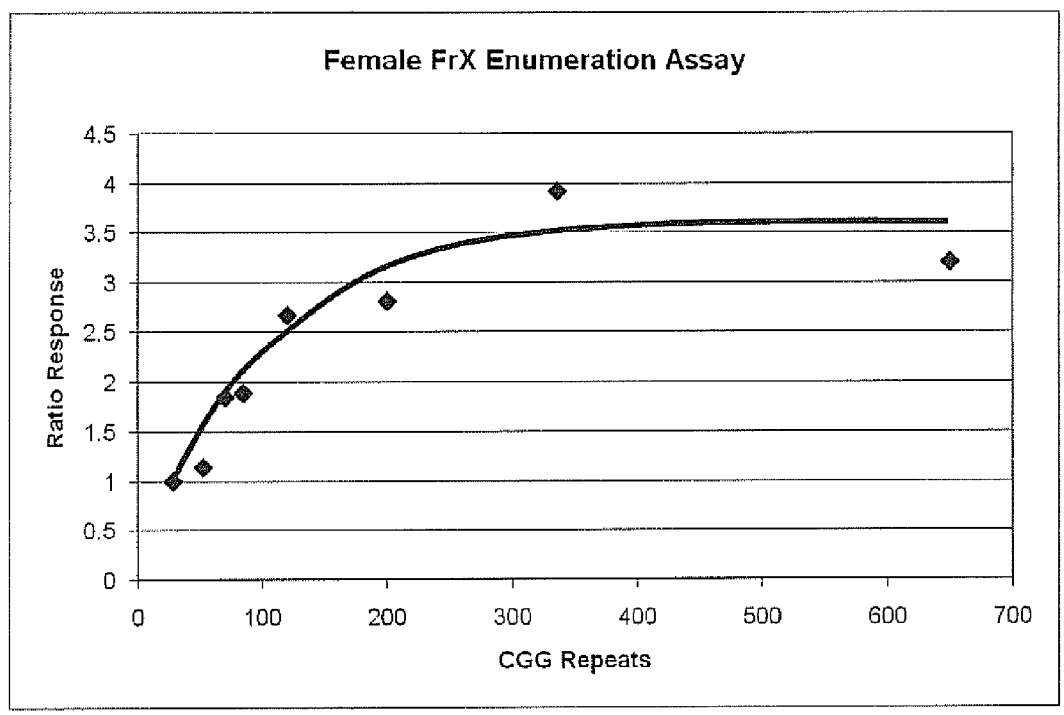

FIG. 12C is data from a second example trinucleotide enumeration assay according to the process outlined in FIGS. 1C and 11. The values along the horizontal axis are the number of CGG repeats according to the supplier of cell line DNA samples. The samples represent females with Fragile X repeat lengths in their longer alleles of between about 29 to about 650. The values along the vertical axis of the plot are the ratio of the fluorescent signal generated by the repeat-detection label divided by the fluorescent signal of amplified target DNA (derived from target-detection label) of the same sample. The ratio data increases monotonically with repeat length well into the full mutation (repeats greater than 200) range.

Below are protocols for experimental steps useful when determining the length of a multinucleotide repeat region of a Fragile X gene target DNA molecule, using labeled deoxynucleotides during amplification of the DNA, and utilizing a second exemplary assay process.

The PCR was performed using the Asuragen Human FMR1 PCR Reagents (Asuragen, Austin Tex.) using their standard protocol, with the addition of 1 µl of 100 µM biotin-dCTP into 20 µl of the kit's PCR reaction mix. The enumeration assay was performed using the same materials and methods of Example 5 above, except for the hybridization buffer was made as described below.

| Component | Amount | Final Concentration |
|---|---|---|
| 50% Dextran Sulfate | 2.15 g | 8.3% |
| Formamide | 5 ml | 50% |
| 20× SSC | 1 ml | 2× |
| H₂0 | 2.37 ml | |
| Total | 10 ml | |

The dextran sulfate was Millipore S4030 (Millipore, Bedford Mass.), the formamide was Millipore S4117, and the SSC was Sigma-Aldrich S6639. This hybridization was also performed at 60° C. for 60 minutes.

Any patents or publications mentioned in this specification are incorporated herein by reference to the same extent as if each individual publication is specifically and individually indicated to be incorporated by reference. U.S. Provisional Patent Application Ser. Nos. 61/224,651, filed Jul. 10, 2009 and 61/288,518, filed Dec. 21, 2009, are hereby incorporated herein by reference in their entirety.

The compositions and methods described herein are presently representative of preferred embodiments, exemplary, and not intended as limitations on the scope of the invention. Changes therein and other uses will occur to those skilled in the art. Such changes and other uses can be made without departing from the scope of the invention as set forth in the claims.

The invention claimed is:

1. A method of determining the length of a multinucleotide repeat region in a target nucleic acid, comprising:

amplifying a target nucleic acid to produce amplified target nucleic acids;

labeling the amplified target nucleic acids with a first label, the first label independent of the number of multinucleotide repeats;

binding the amplified target nucleic acids to a first capture probe specific for the amplified target nucleic acids, the first capture probe attached to a first encoded particle characterized by a first code;

amplifying the target nucleic acid to produce multinucleotide repeat region nucleic acids;

labeling the multinucleotide repeat region nucleic acids with a second label, the second label proportional to the number of multinucleotide repeats;

binding the multinucleotide repeat region nucleic acids to a second capture probe specific for the multinucleotide repeat region nucleic acids, the second capture probe attached to a second encoded particle characterized by a second code, wherein the first and second codes are distinguishable;

detecting the first code and the first label associated with the first capture probe to produce a first signal;

detecting the second code and the second label associated with the second capture probe to produce a second signal; and determining a ratio of the first signal and the second signal, wherein the ratio is indicative of the length of the multinucleotide repeat in the target nucleic acid.

2. The method of claim 1, wherein the second label is present in nucleotides used in amplifying the target nucleic acid to produce the multinucleotide repeat region nucleic acids.

3. The method of claim 1, wherein the second label is present in the second capture probe.

4. The method of claim 3, wherein the first and/or second capture probe is a nucleic acid probe.

5. The method of claim 1, wherein the target nucleic acid is isolated from a biological sample.

6. The method of claim 1, wherein the target nucleic acid is genomic DNA.

7. The method of claim 5, wherein the biological sample is obtained from an individual subject.

8. The method of claim 5, wherein the individual subject is human.

9. The method of claim 6, wherein the individual subject has or is at risk of having a trinucleotide repeat expansion disorder selected from the group consisting of:

Dentatorubropallidoluysian atrophy, Huntington's disease, spinobulbar muscular atrophy, spinocerebellar ataxia type 1, spinocerebellar ataxia type 2, spinocerebellar ataxia type 3, spinocerebellar ataxia type 6, spinocerebellar ataxia type 7, spinocerebellar ataxia type 17, fragile X syndrome; fragile XE mental retardation; Friedreich's ataxia; myotonic dystrophy; spinocerebellar ataxia type 8 and spinocerebellar ataxia type 12.

10. The method of claim 1, further comprising:

amplifying a reference nucleic acid multinucleotide repeat region to produce amplified target reference nucleic acids;

labeling the amplified target reference nucleic acids with a first label and a second label, the first label independent of the number of multinucleotide repeats and the second label proportional to the number of multinucleotide repeats, wherein the first and second labels are each independently incorporated in the amplified target reference nucleic acids during the amplifying or after the amplifying;

binding the amplified target reference nucleic acids to a capture probe specific for the amplified target reference nucleic acids;

detecting the first label associated with the capture probe to produce a third signal;

detecting the second label associated with the capture probe to produce a fourth signal;

determining a ratio of the third signal and the fourth signal, wherein the ratio is indicative of the length of the multinucleotide repeat region in the target reference nucleic acid; and comparing ratio of the first signal and the second signal with the ratio of the third signal and the fourth signal.

11. The method of claim 1, further comprising:

amplifying a second target nucleic acid to produce amplified second target nucleic acids;

labeling the amplified second target nucleic acids with a first label and a second label, the first label independent of the number of multinucleotide repeats and the second label proportional to the number of multinucleotide repeats;

binding the amplified second target nucleic acids to a capture probe specific for the amplified second target nucleic acids;

detecting the first label associated with the capture probe to produce a first signal;

detecting the second label associated with the capture probe to produce a second signal; and determining a ratio of the first signal and the second signal, wherein the ratio is indicative of the length of the multinucleotide repeat in the second target nucleic acid.

12. The method of claim 1, wherein the first and second encoded particles are present together in a reaction vessel during binding of the amplified target nucleic acids and nucleic acids to the first and second capture probes.

13. The method of claim 1, wherein the first and second capture probes are different.

14. A method of screening an individual for a genetic condition characterized by an altered multinucleotide repeat region in a target nucleic acid, comprising:

amplifying from a sample obtained from the individual a target nucleic acid to produce amplified target nucleic acids;

labeling the amplified target nucleic acids with a first label, the first label independent of the number of multinucleotide repeats;

binding the amplified target nucleic acids to a first capture probe specific for the amplified target nucleic acids, the first capture probe attached to a first encoded particle characterized by a first code;

amplifying the target nucleic acid to produce multinucleotide repeat region nucleic acids;

labeling the multinucleotide repeat region nucleic acids with a second label, the second label proportional to the number of multinucleotide repeats;

binding the multinucleotide repeat region nucleic acids to a second capture probe specific for the multinucleotide repeat region nucleic acids, the second capture probe attached to a second encoded particle characterized by a second code, wherein the first and second codes are distinguishable;

detecting the first code and the first label associated with the first capture probe to produce a first signal;

detecting the second code and the second label associated with the second capture probe to produce a second signal; and determining a ratio of the first signal and the second signal, wherein the ratio is indicative of the length of the multinucleotide repeat in the target nucleic acid.

* * * * *

UNITED STATES PATENT AND TRADEMARK OFFICE
CERTIFICATE OF CORRECTION

| | | |
|---|---|---|
| PATENT NO. | : 8,592,158 B2 | Page 1 of 1 |
| APPLICATION NO. | : 12/834633 | |
| DATED | : November 26, 2013 | |
| INVENTOR(S) | : Karl Edwin Adler, Jr. | |

It is certified that error appears in the above-identified patent and that said Letters Patent is hereby corrected as shown below:

In the Claims:

Column 37, line 25, after "claim," replace "5" with --7.--

Signed and Sealed this
Twenty-ninth Day of July, 2014

Michelle K. Lee
*Deputy Director of the United States Patent and Trademark Office*

SEQUENCE LISTING

<160> NUMBER OF SEQ ID NOS: 18

<210> SEQ ID NO 1
<211> LENGTH: 30
<212> TYPE: DNA
<213> ORGANISM: artificial

```
<220> FEATURE:
<223> OTHER INFORMATION: primer to amplify a target nucleic acid
      including a multinucleotide repeat region present in the FMR1 gene

<400> SEQUENCE: 1
ggaacagcgt tgatcacgtg acgtggtttc                                    30

<210> SEQ ID NO 2
<211> LENGTH: 29
<212> TYPE: DNA
<213> ORGANISM: artificial
<220> FEATURE:
<223> OTHER INFORMATION: primer to amplify a target nucleic acid
      including a multinucleotide repeat region present in the FMR1 gene

<400> SEQUENCE: 2
ggggcctgcc ctagagccaa gtaccttgt                                     29

<210> SEQ ID NO 3
<211> LENGTH: 21
<212> TYPE: DNA
<213> ORGANISM: artificial
<220> FEATURE:
<223> OTHER INFORMATION: primer to amplify a target nucleic acid
      including a multinucleotide repeat region present in the FMR1 gene

<400> SEQUENCE: 3
gacggaggcg cccgtgccag g                                             21

<210> SEQ ID NO 4
<211> LENGTH: 23
<212> TYPE: DNA
<213> ORGANISM: artificial
<220> FEATURE:
<223> OTHER INFORMATION: primer to amplify a target nucleic acid
      including a multinucleotide repeat region present in the FMR1 gene

<400> SEQUENCE: 4
tcctccatct tctcttcagc cct                                           23

<210> SEQ ID NO 5
<211> LENGTH: 30
<212> TYPE: DNA
<213> ORGANISM: artificial
<220> FEATURE:
<223> OTHER INFORMATION: primer to amplify a target nucleic acid
      including a multinucleotide repeat region present in the FMR1 gene

<400> SEQUENCE: 5
tgacggaggc gccgctgcca gggggcgtgc                                    30

<210> SEQ ID NO 6
<211> LENGTH: 30
<212> TYPE: DNA
<213> ORGANISM: artificial
<220> FEATURE:
<223> OTHER INFORMATION: primer to amplify a target nucleic acid
      including a multinucleotide repeat region present in the FMR1 gene

<400> SEQUENCE: 6
gagaggtggg ctgcgggcgc tcgaggccca                                    30

<210> SEQ ID NO 7
<211> LENGTH: 30
<212> TYPE: DNA
<213> ORGANISM: artificial
<220> FEATURE:
<223> OTHER INFORMATION: primer to amplify a target nucleic acid
``` including a multinucleotide repeat region present in the FMR1 gene

<400> SEQUENCE: 7
aggcgctcag ctccgtttcg gtttcacttc                                    30

<210> SEQ ID NO 8
<211> LENGTH: 21
<212> TYPE: DNA
<213> ORGANISM: artificial
<220> FEATURE:
<223> OTHER INFORMATION: primer to amplify a target nucleic acid
      including a multinucleotide repeat region present in the FMR1 gene

<400> SEQUENCE: 8
gtgggctgcg ggcgctcgag g                                             21

<210> SEQ ID NO 9
<211> LENGTH: 30
<212> TYPE: DNA
<213> ORGANISM: artificial
<220> FEATURE:
<223> OTHER INFORMATION: primer to amplify a target nucleic acid
      including a multinucleotide repeat region present in the FMR1 gene

<400> SEQUENCE: 9
gctcagctcc gtttcggttt cacttccggt                                    30

<210> SEQ ID NO 10
<211> LENGTH: 30
<212> TYPE: DNA
<213> ORGANISM: artificial
<220> FEATURE:
<223> OTHER INFORMATION: primer to amplify a target nucleic acid
      including a multinucleotide repeat region present in the FMR1 gene

<400> SEQUENCE: 10
agccccgcac ttccaccacc agctcctcca                                    30

<210> SEQ ID NO 11
<211> LENGTH: 21
<212> TYPE: DNA
<213> ORGANISM: artificial
<220> FEATURE:
<223> OTHER INFORMATION: primer to amplify a target nucleic acid
      including a multinucleotide repeat region present in the FMR1 gene

<400> SEQUENCE: 11
gacggaggcg ccgctgccag g                                             21

<210> SEQ ID NO 12
<211> LENGTH: 21
<212> TYPE: DNA
<213> ORGANISM: artificial
<220> FEATURE:
<223> OTHER INFORMATION: primer to amplify a target nucleic acid
      including a multinucleotide repeat region present in the FMR1 gene

<400> SEQUENCE: 12
gtgggctgcg ggcgctcgag g                                             21

<210> SEQ ID NO 13
<211> LENGTH: 21
<212> TYPE: DNA
<213> ORGANISM: artificial
<220> FEATURE:
<223> OTHER INFORMATION: primer to amplify a target nucleic acid
      including a multinucleotide repeat region present in the FMR1 gene

```
<400> SEQUENCE: 13
gtgacggagg cgccgctgcc a                                          21

<210> SEQ ID NO 14
<211> LENGTH: 30
<212> TYPE: DNA
<213> ORGANISM: artificial
<220> FEATURE:
<223> OTHER INFORMATION: primer to amplify a target nucleic acid
      including a multinucleotide repeat region present in the FMR1 gene

<400> SEQUENCE: 14
agctcctcca tcttctcttc agccctgcta                                 30

<210> SEQ ID NO 15
<211> LENGTH: 24
<212> TYPE: DNA
<213> ORGANISM: artificial
<220> FEATURE:
<223> OTHER INFORMATION: primer to amplify a target nucleic acid
      including a multinucleotide repeat region present in the FMR1 gene

<400> SEQUENCE: 15
ctcgaggccc agccgccgcc gccg                                       24

<210> SEQ ID NO 16
<211> LENGTH: 22
<212> TYPE: DNA
<213> ORGANISM: artificial
<220> FEATURE:
<223> OTHER INFORMATION: Capture probe

<400> SEQUENCE: 16
ctggcagcgg cgcctccgtc ac                                         22

<210> SEQ ID NO 17
<211> LENGTH: 12
<212> TYPE: DNA
<213> ORGANISM: artificial
<220> FEATURE:
<223> OTHER INFORMATION: repeat motif reporter probe

<400> SEQUENCE: 17
ccgccgccgc cg                                                    12

<210> SEQ ID NO 18
<211> LENGTH: 15
<212> TYPE: DNA
<213> ORGANISM: artificial
<220> FEATURE:
<223> OTHER INFORMATION: Capture probe

<400> SEQUENCE: 18
cggcggcggc ggcgg                                                 15
```